(12) United States Patent
Bosteels et al.

(10) Patent No.: US 11,254,753 B2
(45) Date of Patent: Feb. 22, 2022

(54) ANTIBODIES WITH REDUCED BINDING TO PROCESS IMPURITIES

(71) Applicant: GlaxoSmithKline Intellectual Property Development Limited, Middlesex (GB)

(72) Inventors: Hella Bosteels, Stevenage (GB); Shugui Chen, Collegeville, PA (US); Kayeleigh Farrow, Stevenage (GB); Richard Kucia-Tran, Stevenage (GB); William John Kenneth Lewis, Stevenage (GB); Andrew S. Thomson, Collegeville, PA (US); Mark Uden, Stevenage (GB)

(73) Assignee: GLAXOSMITHKLINE INTELLECTUAL PROPERTY DEVELOPMENT LIMITED

(*) Notice: Subject to any disclaimer, the term of this patent is extended or adjusted under 35 U.S.C. 154(b) by 280 days.

(21) Appl. No.: 16/339,027

(22) PCT Filed: Oct. 3, 2017

(86) PCT No.: PCT/EP2017/075038
§ 371 (c)(1),
(2) Date: Apr. 3, 2019

(87) PCT Pub. No.: WO2018/065389
PCT Pub. Date: Apr. 12, 2018

(65) Prior Publication Data
US 2019/0225708 A1    Jul. 25, 2019

Related U.S. Application Data

(60) Provisional application No. 62/404,849, filed on Oct. 6, 2016.

(51) Int. Cl.
*C07K 16/40*    (2006.01)
*C07K 16/00*    (2006.01)

(52) U.S. Cl.
CPC ........... *C07K 16/40* (2013.01); *C07K 16/00* (2013.01); *C07K 2317/522* (2013.01); *C07K 2317/53* (2013.01); *C07K 2317/92* (2013.01)

(58) Field of Classification Search
CPC .............. C07K 16/00; C07K 2317/53; C07K 2317/92; C07K 2317/522
See application file for complete search history.

(56) References Cited

U.S. PATENT DOCUMENTS

| 2013/0323236 | A1* | 12/2013 | Humphreys | ............ | A61P 29/00 |
| | | | | | 424/133.1 |
| 2015/0017169 | A1* | 1/2015 | Humphreys | ............ | A61P 37/02 |
| | | | | | 424/136.1 |
| 2015/0018529 | A1* | 1/2015 | Humphreys | ......... | C07K 16/468 |
| | | | | | 530/387.3 |
| 2016/0320391 | A1* | 11/2016 | Gunawan | ............ | G01N 33/573 |

FOREIGN PATENT DOCUMENTS

| WO | WO 2011/066501 A1 | 6/2011 |
| WO | WO 2015/038888 A1 | 3/2015 |

OTHER PUBLICATIONS

Peters, et al., "Engineering an Improved IgG4 Molecule with Reduced Disulfide Bond Heterogeneity and Increased Fab Domain Thermal Stability", *Journal of Biological Chemistry*, 287(29):24525-24533 (2012).
Scapin Giovanna et al: "Structure of 1-9 full-length human anti-PDI therapeutic IgG4 antibody pembrolizumab", Nature Structural & Molecular Biology, 22(12):953-958 (2015).
Tran Benjamin et al: "Investigating 1-20 interactions between phospholipase B-Like 2 and antibodies during Protein A chromatography", Journal of Chromatography, 1438:31-38 (2016).
Colman P. M., Effects of amino acid sequence changes on antibody-antigen interactions, Research in Immunology, 1994, v. 145, No. 1, pp. 33-36, p. 33). Amino acid substitutions ou.
Safdari Y. et al., Antibody humanization methods- a review and update, Biotechnology and Genetic Engineering Reviews, 2013, v. 29, No. 2, pp. 175-186, pp. 178,180.
Torres M. et al., The immunoglobulin constant region contributes to affinity and specificity, Trends in immunology, 2008, v. 29, No. 2, pp. 91-97, pp. 93-94.
Muller S. et al., Spliceosomal peptideP140 for immunotherapy of systemic lupus erythematosus: results of an early phase II clinical trial, Arthritis & Rheumatism: Official Jou.

* cited by examiner

*Primary Examiner* — Sharon X Wen
(74) *Attorney, Agent, or Firm* — Craig T. Ajmo; J. Scott Young

(57) ABSTRACT

The present invention relates to variant antibodies and methods of generating said antibodies with a reduced level of binding to process impurities. In particular, the invention describes variant IgG4 antibodies which have been modified in the heavy chain constant region at any one or a combination of amino acids in the region between Kabat residues 203 and 256, wherein the variant IgG4 antibody has a reduced level of binding to host cell protein (HCP), compared to an unmodified IgG4 antibody. The invention also relates to compositions comprising said variant IgG4 antibodies.

14 Claims, 11 Drawing Sheets
Specification includes a Sequence Listing.

Figure 2
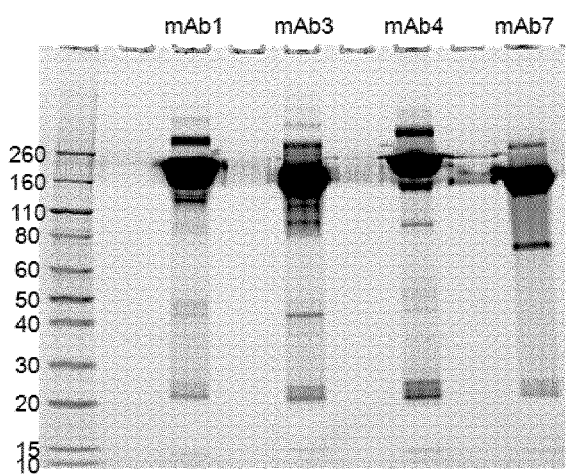 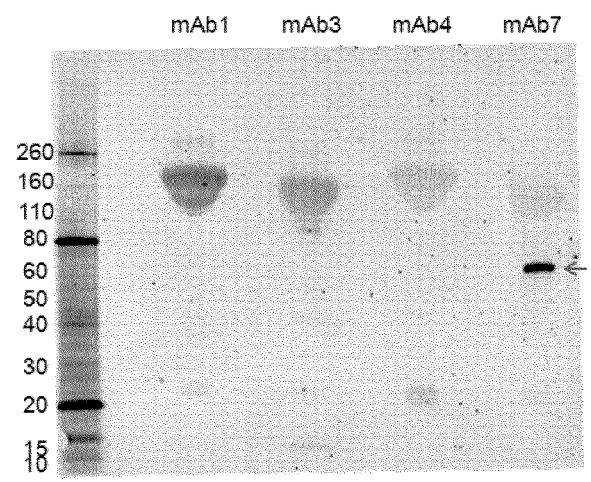

Figure 3
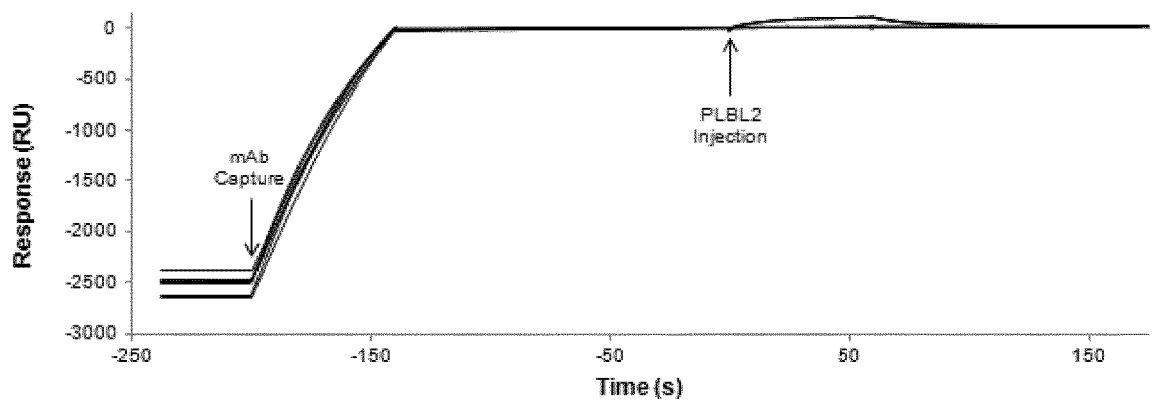
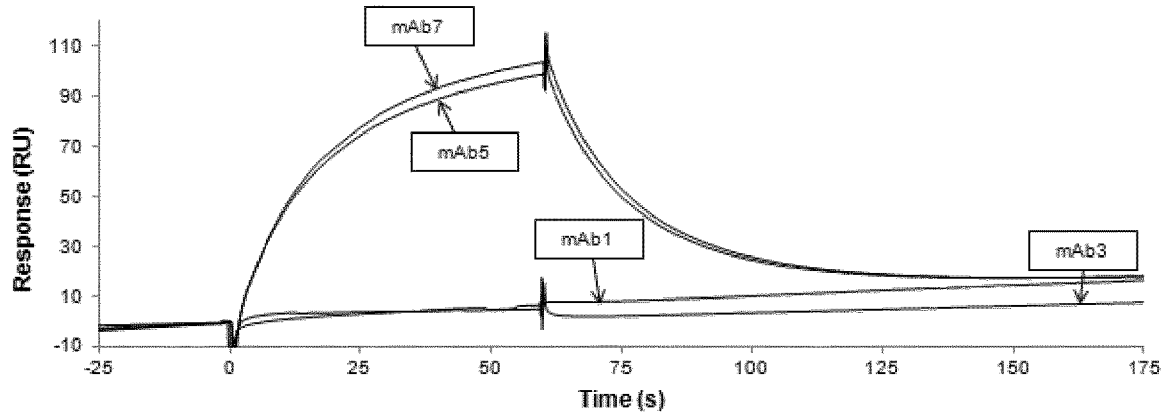
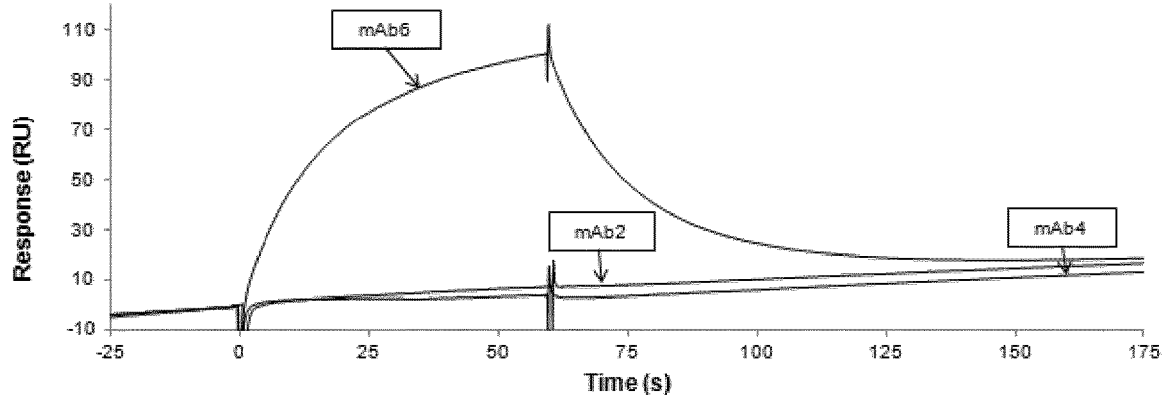

Figure 4
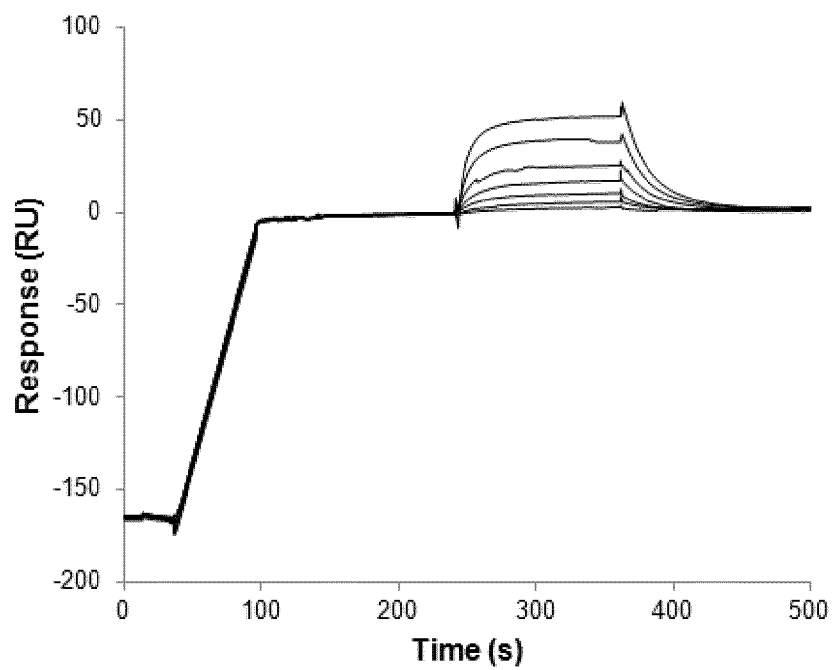
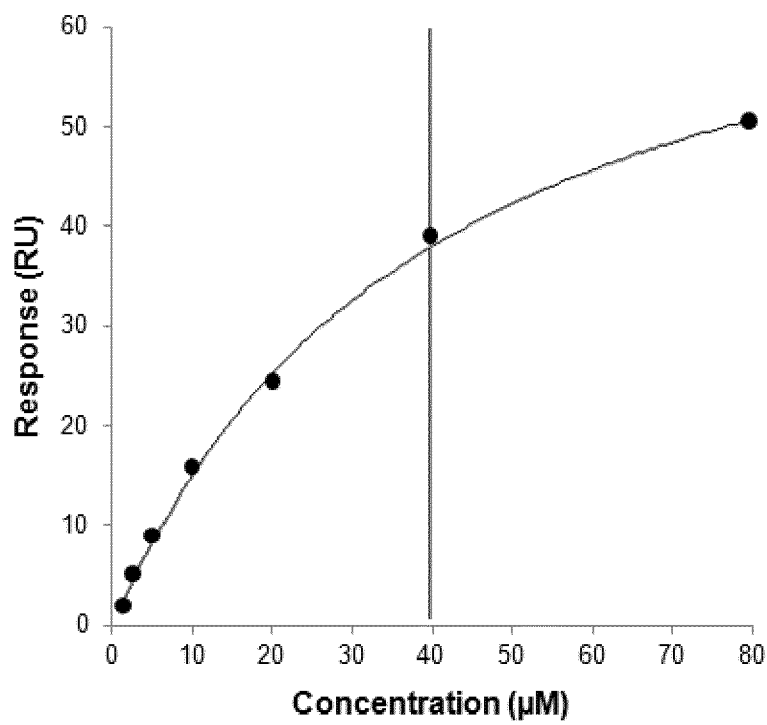

Figure 6:
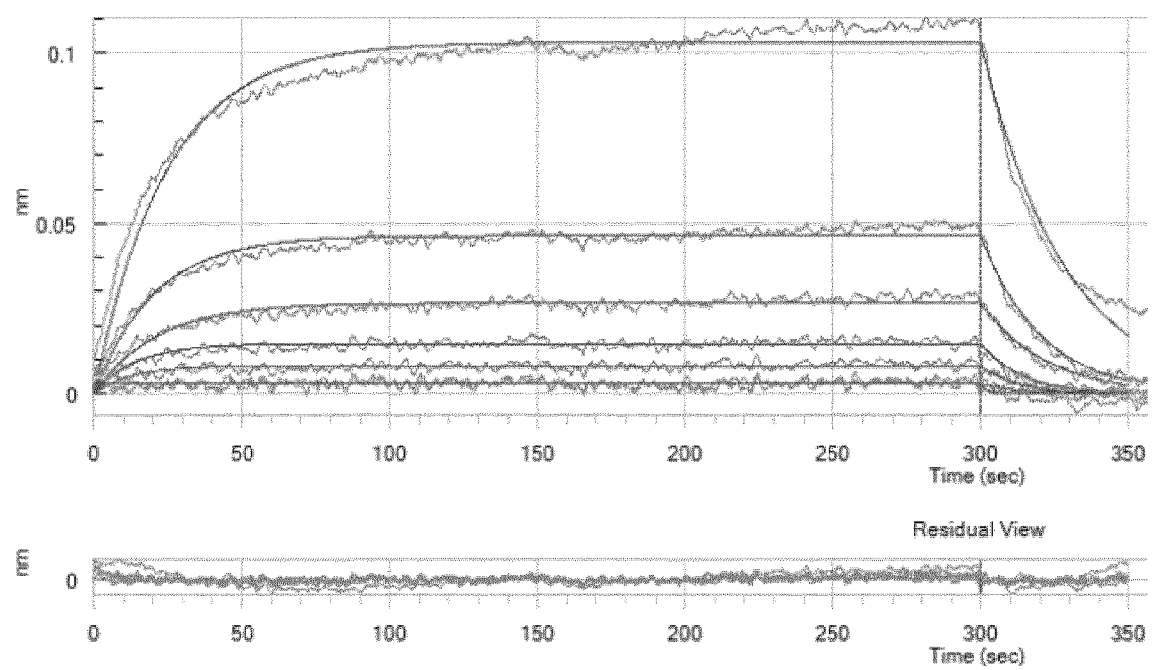

Figure 6
A
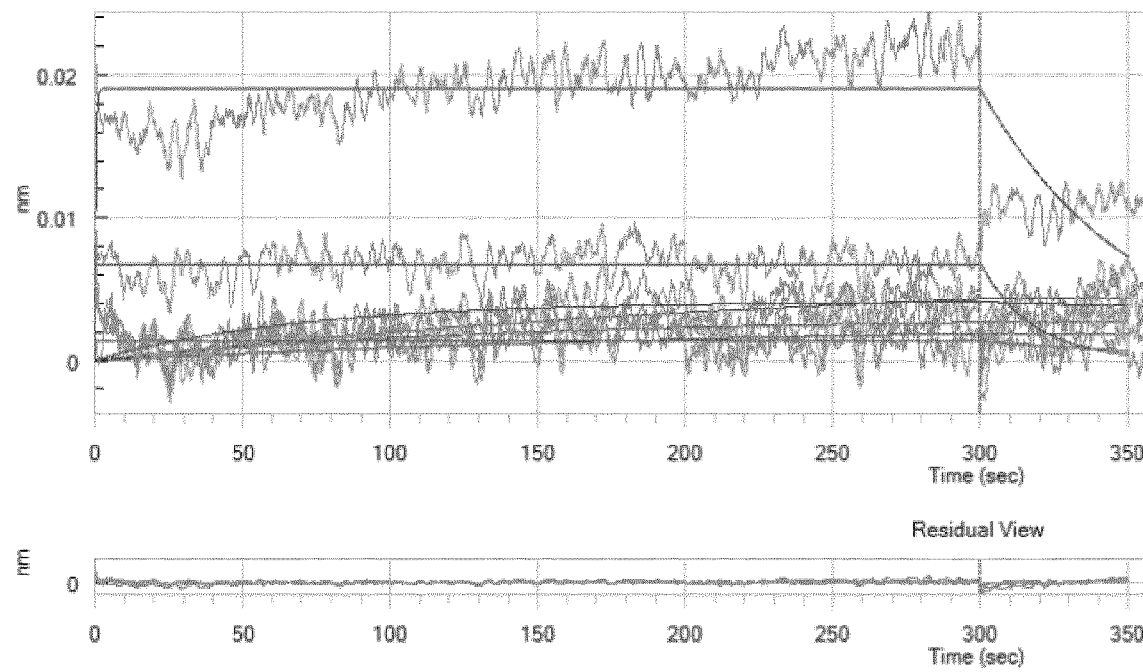
B
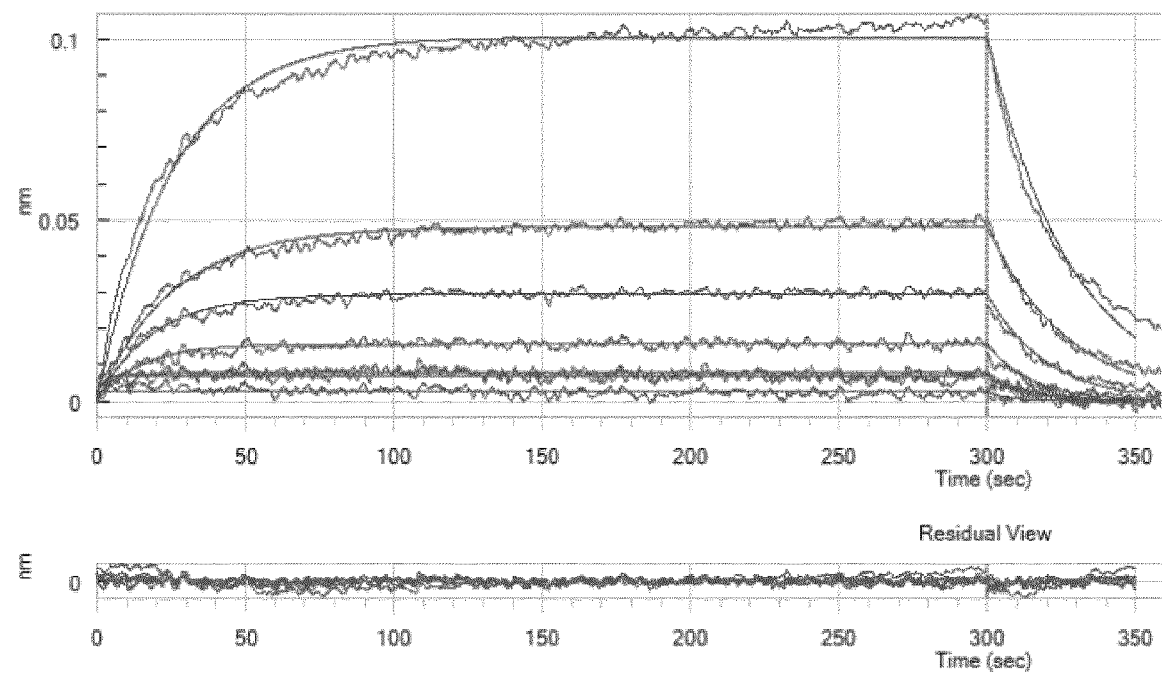

C

Figure 8

CH1

| # | SEQ ID NO. | KABAT | 188 | 189 | 190 | 191 | 192 | 193 | 194 | 195 | 196 | 197 | 198 | 199 | 200 | 203 | 205 | 206 | 207 | 208 | 209 | 210 | 211 | 212 | 213 | 214 | 215 | 216 | 217 | 218 | 219 | 220 | 221 | 222 | 223 |
|---|---|---|---|---|---|---|---|---|---|---|---|---|---|---|---|---|---|---|---|---|---|---|---|---|---|---|---|---|---|---|---|---|---|---|---|---|
| mAb1 | IgG1 | | S | S | V | T | T | V | P | S | S | S | L | G | T | Q | T | Y | I | C | N | V | N | H | K | P | S | N | T | K | V | D | K | K | V |
| mAb2 | IgG1 | | S | S | V | T | T | V | P | S | S | S | L | G | T | Q | T | Y | I | C | N | V | N | H | K | P | S | N | T | K | V | D | K | K | V |
| mAb3 | IgG2 | | S | S | V | T | T | V | P | S | S | N | F | G | T | Q | T | Y | T | C | N | V | D | H | K | P | S | N | T | K | V | D | K | T | V |
| mAb4 | IgG2/4 | | S | S | V | T | T | V | P | S | S | N | F | G | T | Q | T | Y | T | C | N | V | D | H | K | P | S | N | T | K | V | D | K | T | V |
| mAb5 | IgG4 | | S | S | V | T | T | V | P | S | S | S | L | G | T | K | T | Y | T | C | N | V | D | H | K | P | S | N | T | K | V | D | K | R | V |
| mAb6 | IgG4 | | S | S | V | T | T | V | P | S | S | S | L | G | T | K | T | Y | T | C | N | V | D | H | K | P | S | N | T | K | V | D | K | R | V |
| mAb7 | IgG4 | | S | S | V | T | T | V | P | S | S | S | L | G | T | K | T | Y | T | C | N | V | D | H | K | P | S | N | T | K | V | D | K | R | V |
| Human | IgG1 | | S | S | V | T | V | P | S | S | S | L | G | T | Q | T | Y | I | C | N | V | N | H | K | P | S | N | T | K | V | D | K | K | V |
| Germline | IgG2 | | S | S | V | T | V | P | S | S | N | F | G | T | Q | T | Y | T | C | N | V | D | H | K | P | S | N | T | K | V | D | K | T | V |
| | IgG4 | | S | S | V | T | V | P | S | S | S | L | G | T | K | T | Y | T | C | N | V | D | H | K | P | S | N | T | K | V | D | K | R | V |

HINGE

| # | SEQ ID NO. | KABAT | 226 | 227 | 228 | 229 | 230 | 232 | 233 | 234 | 235 | 236 | 237 | 238 | 239 | 240 | 241 | 242 | 243 |
|---|---|---|---|---|---|---|---|---|---|---|---|---|---|---|---|---|---|---|---|---|
| mAb1 | IgG1 | | E | P | K | | | S | C | D | K | T | H | T | C | P | P | C | P |
| mAb2 | IgG1 | | E | P | K | | | S | C | D | K | T | H | T | C | P | P | C | P |
| mAb3 | IgG2 | | E | P | K | | | C | C | | V | | E | | C | P | P | C | P |
| mAb4 | IgG2/4 | | E | R | K | | | C | C | | V | | E | | C | P | P | C | P |
| mAb5 | IgG4 | | E | S | K | Y | G | | | | | | | P | C | P | P | C | P |
| mAb6 | IgG4 | | E | S | K | Y | G | | | | | | | P | C | P | P | C | P |
| mAb7 | IgG4 | | E | S | K | Y | G | | | | | | | P | C | P | P | C | P |
| Human | IgG1 | | E | P | K | | | S | C | D | K | T | H | T | C | P | P | C | P |
| Germline | IgG2 | | E | R | K | | | C | C | | V | | E | | C | P | P | C | P |
| | IgG4 | | E | S | K | Y | G | | | | | | | P | C | P | S | C | P |

CH2

| # | SEQ ID NO. | KABAT | 244 | 245 | 246 | 247 | 248 | 249 | 250 | 251 | 252 | 253 | 254 | 255 | 256 |
|---|---|---|---|---|---|---|---|---|---|---|---|---|---|---|---|
| mAb1 | IgG1 | | A | P | E | L | L | G | G | P | S | V | F | L | F |
| mAb2 | IgG1 | | A | P | E | L | L | G | G | P | S | V | F | L | F |
| mAb3 | IgG2 | | A | P | P | | A | A | A | S | S | V | F | L | F |
| mAb4 | IgG2/4 | | A | P | P | | A | A | A | S | S | V | F | L | F |
| mAb5 | IgG4 | | A | P | E | F | E | G | A | P | S | V | F | L | F |
| mAb6 | IgG4 | | A | P | P | | A | A | A | P | S | V | F | L | F |
| mAb7 | IgG4 | | A | P | E | F | E | G | A | P | S | V | F | L | F |
| Human | IgG1 | | A | P | E | L | L | G | G | P | S | V | F | L | F |
| Germline | IgG2 | | A | P | P | V | V | A | G | P | S | V | F | L | F |
| | IgG4 | | A | P | E | F | L | G | G | P | S | V | F | L | F |

Sequence difference
Considered of interest in relation to PLBL2 binding
Mutated - Different from Human sequence

Figure 9

SEQUENCE LISTING

```
<160> NUMBER OF SEQ ID NOS: 38

<210> SEQ ID NO 1
<211> LENGTH: 61
<212> TYPE: PRT
<213> ORGANISM: Human

<400> SEQUENCE: 1

Ser Ser Val Val Thr Val Pro Ser Ser Leu Gly Thr Gln Thr Tyr
1               5                   10                  15

Ile Cys Asn Val Asn His Lys Pro Ser Asn Thr Lys Val Asp Lys Lys
                20                  25                  30

Val Glu Pro Lys Ser Cys Asp Lys Thr His Thr Cys Pro Pro Cys Pro
            35                  40                  45

Ala Pro Glu Leu Leu Gly Gly Pro Ser Val Phe Leu Phe
        50                  55                  60

<210> SEQ ID NO 2
<211> LENGTH: 61
<212> TYPE: PRT
<213> ORGANISM: Human

<400> SEQUENCE: 2

Ser Ser Val Val Thr Val Pro Ser Ser Leu Gly Thr Gln Thr Tyr
1               5                   10                  15

Ile Cys Asn Val Asn His Lys Pro Ser Asn Thr Lys Val Asp Lys Lys
                20                  25                  30

Val Glu Pro Lys Ser Cys Asp Lys Thr His Thr Cys Pro Pro Cys Pro
            35                  40                  45

Ala Pro Glu Leu Leu Gly Gly Pro Ser Val Phe Leu Phe
        50                  55                  60

<210> SEQ ID NO 3
<211> LENGTH: 57
<212> TYPE: PRT
<213> ORGANISM: Artificial
<220> FEATURE:
<223> OTHER INFORMATION: mAb3 (IgG2)

<400> SEQUENCE: 3

Ser Ser Val Val Thr Val Pro Ser Ser Asn Phe Gly Thr Gln Thr Tyr
1               5                   10                  15

Thr Cys Asn Val Asp His Lys Pro Ser Asn Thr Lys Val Asp Lys Thr
                20                  25                  30

Val Glu Arg Lys Cys Cys Val Glu Cys Pro Pro Cys Pro Ala Pro Pro
            35                  40                  45

Ala Ala Ala Ser Ser Val Phe Leu Phe
        50                  55

<210> SEQ ID NO 4
<211> LENGTH: 57
<212> TYPE: PRT
<213> ORGANISM: Artificial
<220> FEATURE:
```

```
<223> OTHER INFORMATION: mAb4 (IgG2/4)

<400> SEQUENCE: 4

Ser Ser Val Val Thr Val Pro Ser Ser Asn Phe Gly Thr Gln Thr Tyr
1               5                   10                  15

Thr Cys Asn Val Asp His Lys Pro Ser Asn Thr Lys Val Asp Lys Thr
            20                  25                  30

Val Glu Arg Lys Cys Cys Val Glu Cys Pro Pro Cys Pro Ala Pro Pro
        35                  40                  45

Ala Ala Ala Ser Ser Val Phe Leu Phe
    50                  55

<210> SEQ ID NO 5
<211> LENGTH: 58
<212> TYPE: PRT
<213> ORGANISM: Artificial
<220> FEATURE:
<223> OTHER INFORMATION: mAb5 (IgG4)

<400> SEQUENCE: 5

Ser Ser Val Val Thr Val Pro Ser Ser Leu Gly Thr Lys Thr Tyr
1               5                   10                  15

Thr Cys Asn Val Asp His Lys Pro Ser Asn Thr Lys Val Asp Lys Arg
            20                  25                  30

Val Glu Ser Lys Tyr Gly Pro Pro Cys Pro Pro Cys Pro Ala Pro Glu
        35                  40                  45

Phe Glu Gly Gly Pro Ser Val Phe Leu Phe
    50                  55

<210> SEQ ID NO 6
<211> LENGTH: 57
<212> TYPE: PRT
<213> ORGANISM: Artificial
<220> FEATURE:
<223> OTHER INFORMATION: mAb6  (IgG4)

<400> SEQUENCE: 6

Ser Ser Val Val Thr Val Pro Ser Ser Leu Gly Thr Lys Thr Tyr
1               5                   10                  15

Thr Cys Asn Val Asp His Lys Pro Ser Asn Thr Lys Val Asp Lys Arg
            20                  25                  30

Val Glu Ser Lys Tyr Gly Pro Pro Cys Pro Pro Cys Pro Ala Pro Pro
        35                  40                  45

Ala Ala Ala Pro Ser Val Phe Leu Phe
    50                  55

<210> SEQ ID NO 7
<211> LENGTH: 58
<212> TYPE: PRT
<213> ORGANISM: Artificial
<220> FEATURE:
<223> OTHER INFORMATION: mAb7 (IgG4)

<400> SEQUENCE: 7

Ser Ser Val Val Thr Val Pro Ser Ser Leu Gly Thr Lys Thr Tyr
1               5                   10                  15

Thr Cys Asn Val Asp His Lys Pro Ser Asn Thr Lys Val Asp Lys Arg
            20                  25                  30

Val Glu Ser Lys Tyr Gly Pro Pro Cys Pro Pro Cys Pro Ala Pro Glu
        35                  40                  45
```

-continued

```
Phe Glu Gly Gly Pro Ser Val Phe Leu Phe
    50                  55
```

<210> SEQ ID NO 8
<211> LENGTH: 61
<212> TYPE: PRT
<213> ORGANISM: Human

<400> SEQUENCE: 8

```
Ser Ser Val Val Thr Val Pro Ser Ser Leu Gly Thr Gln Thr Tyr
1               5                   10                  15

Ile Cys Asn Val Asn His Lys Pro Ser Asn Thr Lys Val Asp Lys Lys
                20                  25                  30

Val Glu Pro Lys Ser Cys Asp Lys Thr His Thr Cys Pro Pro Cys Pro
            35                  40                  45

Ala Pro Glu Leu Leu Gly Gly Pro Ser Val Phe Leu Phe
        50                  55                  60
```

<210> SEQ ID NO 9
<211> LENGTH: 57
<212> TYPE: PRT
<213> ORGANISM: Human

<400> SEQUENCE: 9

```
Ser Ser Val Val Thr Val Pro Ser Ser Asn Phe Gly Thr Gln Thr Tyr
1               5                   10                  15

Thr Cys Asn Val Asp His Lys Pro Ser Asn Thr Lys Val Asp Lys Thr
                20                  25                  30

Val Glu Arg Lys Cys Cys Val Glu Cys Pro Pro Cys Pro Ala Pro Pro
            35                  40                  45

Val Ala Gly Pro Ser Val Phe Leu Phe
        50                  55
```

<210> SEQ ID NO 10
<211> LENGTH: 58
<212> TYPE: PRT
<213> ORGANISM: Human

<400> SEQUENCE: 10

```
Ser Ser Val Val Thr Val Pro Ser Ser Leu Gly Thr Lys Thr Tyr
1               5                   10                  15

Thr Cys Asn Val Asp His Lys Pro Ser Asn Thr Lys Val Asp Lys Arg
                20                  25                  30

Val Glu Ser Lys Tyr Gly Pro Pro Cys Pro Ser Cys Pro Ala Pro Glu
            35                  40                  45

Phe Leu Gly Gly Pro Ser Val Phe Leu Phe
        50                  55
```

<210> SEQ ID NO 11
<211> LENGTH: 58
<212> TYPE: PRT
<213> ORGANISM: Artificial
<220> FEATURE:
<223> OTHER INFORMATION: mAb5-1B (IgG4)

<400> SEQUENCE: 11

```
Ser Ser Val Val Thr Val Pro Ser Ser Leu Gly Thr Gln Thr Tyr
1               5                   10                  15

Thr Cys Asn Val Asp His Lys Pro Ser Asn Thr Lys Val Asp Lys Arg
                20                  25                  30
```

Val Glu Ser Lys Tyr Gly Pro Pro Cys Pro Cys Pro Ala Pro Glu
         35                  40                  45

Phe Glu Gly Gly Pro Ser Val Phe Leu Phe
         50                  55

<210> SEQ ID NO 12
<211> LENGTH: 58
<212> TYPE: PRT
<213> ORGANISM: Artificial
<220> FEATURE:
<223> OTHER INFORMATION: mAb5-2B (IgG4)

<400> SEQUENCE: 12

Ser Ser Val Val Thr Val Pro Ser Ser Leu Gly Thr Lys Thr Tyr
1               5                   10                  15

Thr Cys Asn Val Asp His Lys Pro Ser Asn Thr Lys Val Asp Lys Lys
             20                  25                  30

Val Glu Ser Lys Tyr Gly Pro Pro Cys Pro Cys Pro Ala Pro Glu
         35                  40                  45

Phe Glu Gly Gly Pro Ser Val Phe Leu Phe
         50                  55

<210> SEQ ID NO 13
<211> LENGTH: 58
<212> TYPE: PRT
<213> ORGANISM: Artificial
<220> FEATURE:
<223> OTHER INFORMATION: mAb5-3B (IgG4)

<400> SEQUENCE: 13

Ser Ser Val Val Thr Val Pro Ser Ser Leu Gly Thr Lys Thr Tyr
1               5                   10                  15

Thr Cys Asn Val Asp His Lys Pro Ser Asn Thr Lys Val Asp Lys Arg
             20                  25                  30

Val Glu Pro Lys Tyr Gly Pro Pro Cys Pro Cys Pro Ala Pro Glu
         35                  40                  45

Phe Glu Gly Gly Pro Ser Val Phe Leu Phe
         50                  55

<210> SEQ ID NO 14
<211> LENGTH: 58
<212> TYPE: PRT
<213> ORGANISM: Artificial
<220> FEATURE:
<223> OTHER INFORMATION: mAb5-4B (IgG4)

<400> SEQUENCE: 14

Ser Ser Val Val Thr Val Pro Ser Ser Leu Gly Thr Lys Thr Tyr
1               5                   10                  15

Thr Cys Asn Val Asp His Lys Pro Ser Asn Thr Lys Val Asp Lys Lys
             20                  25                  30

Val Glu Pro Lys Tyr Gly Pro Pro Cys Pro Cys Pro Ala Pro Glu
         35                  40                  45

Phe Gly Gly Gly Pro Ser Val Phe Leu Phe
         50                  55

<210> SEQ ID NO 15
<211> LENGTH: 58
<212> TYPE: PRT
<213> ORGANISM: Artificial
<220> FEATURE:
<223> OTHER INFORMATION: mAb5-5B (IgG4)

<400> SEQUENCE: 15

Ser Ser Val Val Thr Val Pro Ser Ser Leu Gly Thr Lys Thr Tyr
1               5                   10                  15

Thr Cys Asn Val Asp His Lys Pro Ser Asn Thr Lys Val Asp Lys Arg
            20                  25                  30

Val Glu Ser Lys Cys Cys Val Glu Cys Pro Pro Cys Pro Ala Pro Glu
        35                  40                  45

Phe Glu Gly Gly Pro Ser Val Phe Leu Phe
    50                  55

<210> SEQ ID NO 16
<211> LENGTH: 61
<212> TYPE: PRT
<213> ORGANISM: Artificial
<220> FEATURE:
<223> OTHER INFORMATION: mAb5-6B (IgG4)

<400> SEQUENCE: 16

Ser Ser Val Val Thr Val Pro Ser Ser Leu Gly Thr Lys Thr Tyr
1               5                   10                  15

Thr Cys Asn Val Asp His Lys Pro Ser Asn Thr Lys Val Asp Lys Arg
            20                  25                  30

Val Glu Ser Lys Ser Cys Asp Lys Thr His Thr Cys Pro Pro Cys Pro
        35                  40                  45

Ala Pro Glu Phe Glu Gly Gly Pro Ser Val Phe Leu Phe
    50                  55                  60

<210> SEQ ID NO 17
<211> LENGTH: 58
<212> TYPE: PRT
<213> ORGANISM: Artificial
<220> FEATURE:
<223> OTHER INFORMATION: mAb5-7B (IgG4)

<400> SEQUENCE: 17

Ser Ser Val Val Thr Val Pro Ser Ser Leu Gly Thr Lys Thr Tyr
1               5                   10                  15

Thr Cys Asn Val Asp His Lys Pro Ser Asn Thr Lys Val Asp Lys Arg
            20                  25                  30

Val Leu Ser Lys Tyr Gly Pro Cys Pro Cys Pro Ala Pro Glu
        35                  40                  45

Phe Glu Gly Gly Pro Ser Val Phe Leu Phe
    50                  55

<210> SEQ ID NO 18
<211> LENGTH: 61
<212> TYPE: PRT
<213> ORGANISM: Human

<400> SEQUENCE: 18

Ser Ser Val Val Thr Val Pro Ser Ser Leu Gly Thr Gln Thr Tyr
1               5                   10                  15

Ile Cys Asn Val Asn His Lys Pro Ser Asn Thr Lys Val Asp Lys Lys
            20                  25                  30

Val Glu Pro Lys Ser Cys Asp Lys Thr His Thr Cys Pro Pro Cys Pro
        35                  40                  45

Ala Pro Glu Leu Leu Gly Gly Pro Ser Val Phe Leu Phe
    50                  55                  60

```
<210> SEQ ID NO 19
<211> LENGTH: 4
<212> TYPE: PRT
<213> ORGANISM: Human

<400> SEQUENCE: 19

Cys Pro Ser Cys
1

<210> SEQ ID NO 20
<211> LENGTH: 4
<212> TYPE: PRT
<213> ORGANISM: Human

<400> SEQUENCE: 20

Cys Pro Pro Cys
1

<210> SEQ ID NO 21
<211> LENGTH: 12
<212> TYPE: PRT
<213> ORGANISM: Human

<400> SEQUENCE: 21

Glu Ser Lys Tyr Gly Pro Pro Cys Pro Ser Cys Pro
1               5                   10

<210> SEQ ID NO 22
<211> LENGTH: 12
<212> TYPE: PRT
<213> ORGANISM: Artificial
<220> FEATURE:
<223> OTHER INFORMATION: Unmodified IgG4 antibody hinge (S_P)

<400> SEQUENCE: 22

Glu Ser Lys Tyr Gly Pro Pro Cys Pro Pro Cys Pro
1               5                   10

<210> SEQ ID NO 23
<211> LENGTH: 4
<212> TYPE: PRT
<213> ORGANISM: Human

<400> SEQUENCE: 23

Tyr Gly Pro Pro
1

<210> SEQ ID NO 24
<211> LENGTH: 7
<212> TYPE: PRT
<213> ORGANISM: Human

<400> SEQUENCE: 24

Ser Cys Asp Lys Thr His Thr
1               5

<210> SEQ ID NO 25
<211> LENGTH: 4
<212> TYPE: PRT
<213> ORGANISM: Human

<400> SEQUENCE: 25

Cys Cys Val Glu
1
```

```
<210> SEQ ID NO 26
<211> LENGTH: 7
<212> TYPE: PRT
<213> ORGANISM: Human

<400> SEQUENCE: 26

Glu Ser Lys Tyr Gly Pro Pro
1               5

<210> SEQ ID NO 27
<211> LENGTH: 10
<212> TYPE: PRT
<213> ORGANISM: Human

<400> SEQUENCE: 27

Glu Pro Lys Ser Cys Asp Lys Thr His Thr
1               5                   10

<210> SEQ ID NO 28
<211> LENGTH: 7
<212> TYPE: PRT
<213> ORGANISM: Artificial
<220> FEATURE:
<223> OTHER INFORMATION: Modification of IgG4 Kabat residues 226 to 238

<400> SEQUENCE: 28

Glu Arg Lys Tyr Gly Pro Pro
1               5

<210> SEQ ID NO 29
<211> LENGTH: 7
<212> TYPE: PRT
<213> ORGANISM: Human

<400> SEQUENCE: 29

Glu Arg Lys Cys Cys Val Glu
1               5

<210> SEQ ID NO 30
<211> LENGTH: 12
<212> TYPE: PRT
<213> ORGANISM: Artificial
<220> FEATURE:
<223> OTHER INFORMATION: Modification of IgG4 Kabat residues 226 to 238

<400> SEQUENCE: 30

Glu Leu Lys Thr Pro Leu Gly Asp Thr Thr His Thr
1               5                   10

<210> SEQ ID NO 31
<211> LENGTH: 6
<212> TYPE: PRT
<213> ORGANISM: Human

<400> SEQUENCE: 31

Glu Phe Leu Gly Gly Pro
1               5

<210> SEQ ID NO 32
<211> LENGTH: 5
<212> TYPE: PRT
<213> ORGANISM: Artificial
<220> FEATURE:
<223> OTHER INFORMATION: Modification of IgG4 Kabat residues 246 to 251

<400> SEQUENCE: 32
```

```
Pro Ala Ala Ala Ser
1               5

<210> SEQ ID NO 33
<211> LENGTH: 5
<212> TYPE: PRT
<213> ORGANISM: Artificial
<220> FEATURE:
<223> OTHER INFORMATION: Modification of IgG4 Kabat residues 246 to 251

<400> SEQUENCE: 33

Pro Ala Ala Ala Pro
1               5

<210> SEQ ID NO 34
<211> LENGTH: 61
<212> TYPE: PRT
<213> ORGANISM: Artificial
<220> FEATURE:
<223> OTHER INFORMATION: mAb2-alphaB(IgG1)

<400> SEQUENCE: 34

Ser Ser Val Val Thr Val Pro Ser Ser Leu Gly Thr Gln Thr Tyr
1               5                   10                  15

Ile Cys Asn Val Asn His Lys Pro Ser Asn Thr Lys Val Asp Lys Arg
                20                  25                  30

Val Glu Pro Lys Ser Cys Asp Lys Thr His Thr Cys Pro Pro Cys Pro
            35                  40                  45

Ala Pro Glu Leu Leu Gly Gly Pro Ser Val Phe Leu Phe
        50                  55                  60

<210> SEQ ID NO 35
<211> LENGTH: 58
<212> TYPE: PRT
<213> ORGANISM: Artificial
<220> FEATURE:
<223> OTHER INFORMATION: mAb5-8B(IgG4)

<400> SEQUENCE: 35

Ser Ser Val Val Thr Val Pro Ser Ser Leu Gly Thr Lys Thr Tyr
1               5                   10                  15

Thr Cys Asn Val Asp His Lys Pro Ser Asn Thr Lys Val Asp Lys Thr
                20                  25                  30

Val Glu Ser Lys Tyr Gly Pro Pro Cys Pro Pro Cys Pro Ala Pro Glu
            35                  40                  45

Phe Glu Gly Gly Pro Ser Val Phe Leu Phe
        50                  55

<210> SEQ ID NO 36
<211> LENGTH: 58
<212> TYPE: PRT
<213> ORGANISM: Artificial
<220> FEATURE:
<223> OTHER INFORMATION: mAb7-2B(IgG4)

<400> SEQUENCE: 36

Ser Ser Val Val Thr Val Pro Ser Ser Leu Gly Thr Lys Thr Tyr
1               5                   10                  15

Thr Cys Asn Val Asp His Lys Pro Ser Asn Thr Lys Val Asp Lys Lys
                20                  25                  30

Val Glu Ser Lys Tyr Gly Pro Pro Cys Pro Pro Cys Pro Ala Pro Glu
            35                  40                  45
```

```
<210> SEQ ID NO 37
<211> LENGTH: 58
<212> TYPE: PRT
<213> ORGANISM: Artificial
<220> FEATURE:
<223> OTHER INFORMATION: mAb7-4B (IgG4)

<400> SEQUENCE: 37

Ser Ser Val Val Thr Val Pro Ser Ser Leu Gly Thr Lys Thr Tyr
1               5                   10                  15

Thr Cys Asn Val Asp His Lys Pro Ser Asn Thr Lys Val Asp Lys Lys
            20                  25                  30

Val Glu Pro Lys Tyr Gly Pro Pro Cys Pro Pro Cys Pro Ala Pro Glu
        35                  40                  45

Phe Glu Gly Gly Pro Ser Val Phe Leu Phe
    50                  55

<210> SEQ ID NO 38
<211> LENGTH: 58
<212> TYPE: PRT
<213> ORGANISM: Artificial
<220> FEATURE:
<223> OTHER INFORMATION: mAb7-5B(IgG4)

<400> SEQUENCE: 38

Ser Ser Val Val Thr Val Pro Ser Ser Leu Gly Thr Lys Thr Tyr
1               5                   10                  15

Thr Cys Asn Val Asp His Lys Pro Ser Asn Thr Lys Val Asp Lys Arg
            20                  25                  30

Val Glu Ser Lys Cys Cys Val Glu Cys Pro Pro Cys Pro Ala Pro Glu
        35                  40                  45

Phe Glu Gly Gly Pro Ser Val Phe Leu Phe
    50                  55
```

ANTIBODIES WITH REDUCED BINDING TO PROCESS IMPURITIES

This application is a 371 of International Application No. PCT/EP2017/075038, filed 3 Oct. 2017, which claims priority to U.S. Provisional Application 62/404,849 filed 6 Oct. 2016, all of which are incorporated herein in their entireties.

FIELD OF INVENTION

The present invention relates to novel antibodies which have a reduced ability to bind, through non-specific and/or specific interactions, with manufacturing process impurities such as host cell proteins. More specifically, the invention relates to novel immunoglobulins, which have a reduced ability to bind such manufacturing process impurities, through modifications to the amino acid sequence of antibodies.

BACKGROUND OF INVENTION

Monoclonal antibodies (mAbs) are biopharmaceuticals which are used for the therapeutic treatment of a wide range of diseases. The manufacture of these complex recombinant proteins typically requires the use of a biological host system, which through genetic engineering, is capable of expressing the product in a suitably active form. In this regard mammalian cell lines, such as Chinese Hamster Ovary (CHO) cells, are ubiquitous in their use as hosts for the industrial production of numerous mAb products, since they are capable of folding, assembling and applying appropriate post-translational modifications to these proteins, ensuring their compatibility with human systems.

A consequence, and thereby a key challenge in the use of cell based systems for the production of mAbs, is the need to isolate the product protein from a range of other complex impurities. These are termed process-related impurities and include a diverse range of proteins which are endogenous to the host organism or associated with such cells (such as virus-like-proteins). These so called host cell proteins (HCPs) represent a broad class of molecules, which have the potential to negatively affect both the stability and safety of the biopharmaceutical drug. Some HCPs may possess proteolytic activity which can adversely affect the stability of the product protein. Other HCPs have the potential to cause an immunogenic response in patients if present in the final drug product. For these reasons the clearance of HCPs represents a major challenge for the manufacture of all biopharmaceutical products.

Clearance of host cell proteins is typically achieved through the use of multiple chromatographic purification techniques, utilising orthogonal separation chemistries. Whilst such an approach is typically effective, challenges arise when the product mAb displays some interaction or affinity to one or more of the proteins comprising the HCP population, resulting in co-purification of these HCPs with the product. In such cases a standard approach is to develop suitable chromatography column wash strategies, designed from a physicochemical perspective, to disrupt these interactions. As the propensity for HCP interaction varies between mAb molecules it is generally held that the hypervariable complementarity determining regions (CDRs) of the antibody are primarily responsible for these interactions. However, the precise sequence and structural motifs within these regions which lead to increased interactions has not been elucidated.

Of the five classes of immunoglobulins (Igs), denoted G, A, M, D and E, the majority of mAb biopharmaceuticals fall within the Immunoglobulin G (IgG) class, of which there are four subclasses numbered 1 through 4.

Recently, HCPs such as putative phospholipase B-Like 2 (PLBL2), also known as phospholipase B domain containing protein 2 (PLBD2), have been shown to have an increased propensity to co-purify with certain immunoglobulin variants. The precise reason for this difference in propensity to co-purify with some IgG isotypes but not others is unknown, however previous studies have posited that the interaction between IgGs and PLBL2 is primarily driven by the CDRs, but are facilitated by the features of the IgG4 constant region which differentiate it from the IgG1 subclass (Tran et al. (2016) *J. Chromatogr.* 1438:31-38). However the exact nature of these differences remains unknown. Process impurities such as PLBL2 have the potential to illicit an immune response in patients. Furthermore, lipases such as PLBL2 have been identified as a potential causative agent for the degradation of formulation excipients (Dixit et al., (2016) *J. Pharm. Sci.*, 105(5):1657-66 and US2016/0101181). These excipients are necessary for the stabilisation of the product protein in the final formulation, and their breakdown would compromise the shelf-life and therefore potential safety of the drug. For these reasons, the presence of process impurities and HCPs such as PLBL2 in the final drug product is highly undesirable.

The increased propensity for certain immunoglobulins to interact with HCPs such as PLBL2 has necessitated the development of specialised purification schemes in order to ensure a sufficiently safe final drug product. Such an approach whilst effective, is however not ideal as not only does it increase the associated cost of manufacturing, but also places an increased burden on process validation, and the need to show that the purification process can robustly clear process impurities to acceptable levels. This then also has implications in terms of increased analytical requirements, since PLBL2 has been shown to be difficult to detect through conventional techniques, often requiring the use of bespoke immunoassays (WO2015/038884).

There therefore remains a need for more effectively and cost efficiently reducing the level of HCPs in the final drug product of therapeutic immunoglobulins.

SUMMARY OF INVENTION

According to a first aspect of the invention, there is provided a variant IgG4 antibody which has been modified in the heavy chain constant region at any one or a combination of amino acids in the region between Kabat residues 203 and 256, wherein the variant IgG4 antibody has a reduced level of binding to host cell protein (HCP), compared to an unmodified IgG4 antibody.

According to a further aspect of the invention, there is provided a cell line encoding the variant IgG4 antibody as defined herein.

According to a further aspect of the invention, there is provided a method of modifying an IgG antibody to reduce binding to a process impurity, comprising the steps of:
  a) identifying at least one amino acid involved in the binding of the process impurity; and
  b) creating a variant of the IgG antibody by substituting the amino acid identified as being involved in the binding with the process impurity with a different amino acid.

According to a further aspect of the invention, there is provided a method of producing an IgG4 antibody with reduced binding to host cell protein (HCP) comprising modifying the antibody sequence in the heavy chain constant region at any one or a combination of amino acids in the region between Kabat residues 203 and 256.

According to a further aspect of the invention, there is provided a composition comprising the variant IgG4 antibody as defined herein.

BRIEF DESCRIPTION OF DRAWING/FIGURES

Figure 1:
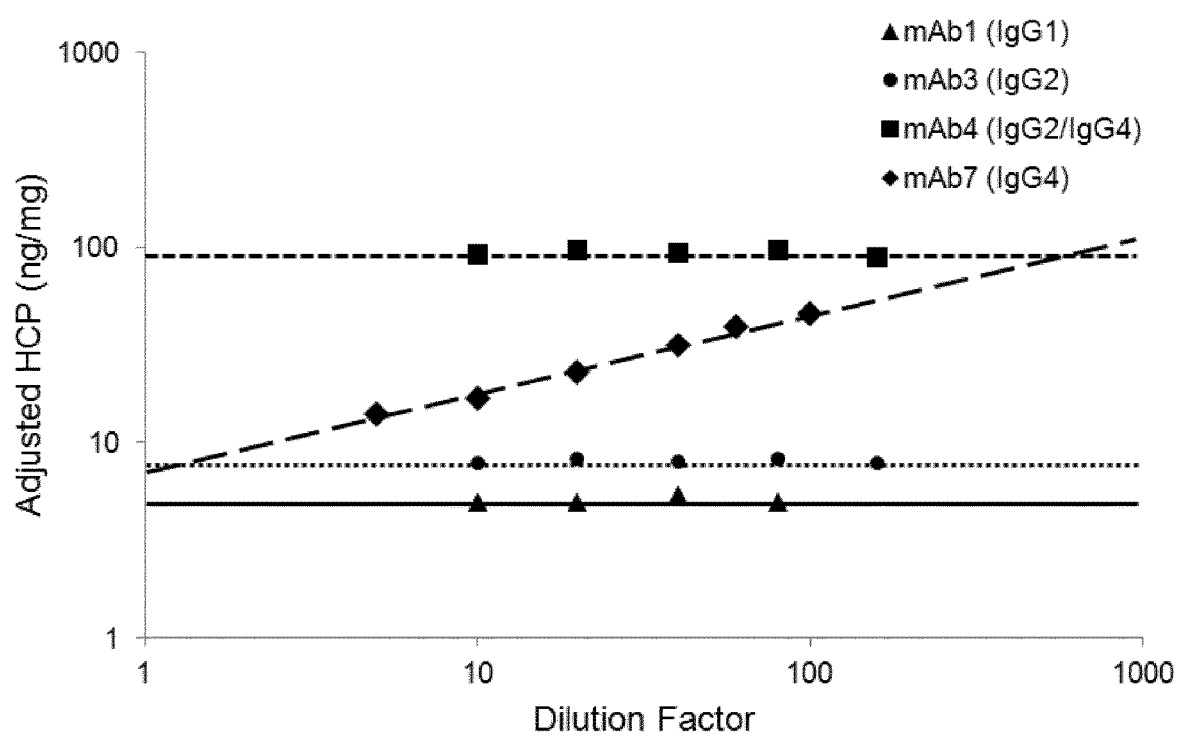

FIG. 1: HCP ELISA Dilutional Linearity of Final Bulk mAbs. Final Bulk samples of humanized IgG products of different subtypes were analyzed by HCP ELISA to assess for dilution non-linearity in the assay. The adjusted HCP values are calculated for each dilution by multiplying the measured HCP concentration by the dilution factor, and then dividing by the product concentration. The adjusted HCP values for each sample dilution are plotted as a function of dilution factor on a log-log scale. Non-linearity is observed when the adjusted HCP value increases with increasing dilution factor. Only mAb7 exhibits non-linearity in the HCP ELISA.

FIG. 2A-B: Anti-PLBL2 Western Blot of different mAbs. Final Bulk samples of humanized IgG products were analyzed by western blot to detect the presence of PLBL2. (A) SyproRUBY stained gel to demonstrate equal loading of samples. (B) Western blot probed with anti-PLBL2 antibodies. PLBL2 is only detected in the mAb7 sample at about 60 kDa, as indicated by the arrow on the right-hand side of the image.

FIG. 3A-C: Binding of PLBL2 to different mAbs by SPR. Surface plasmon resonance (SPR) sensograms of PLBL2 binding to different mAbs. (A) Sensogram demonstrates similar capture levels of all seven mAb by the immobilized anti-Human IgG Fc monoclonal antibody, with mAb injection indicated by arrow at ~−200 seconds, and PLBL2 injection indicated by arrow at 0 seconds. Zoomed sensogram showing PLBL2 binding and dissociation from mAb1, mAb3, mAb5, and mAb7 (B) and mAb2, mAb4, and mAb6 (C), demonstrating that PLBL2 selectively bound to IgG4 molecules.

FIG. 4A-B: PLBL2 binding affinity to mAb7. Surface plasmon resonance binding experiment to calculate the affinity of PLBL2 binding to mAb7. (A) Sensograms show increasing PLBL2 concentrations from 1.25 μM to 80 μM correlate to increased binding to mAb7. (B) Plot of steady state binding response as a function of PLBL2 concentration. 1:1 binding model used to calculate $K_D$.

Figure 5:
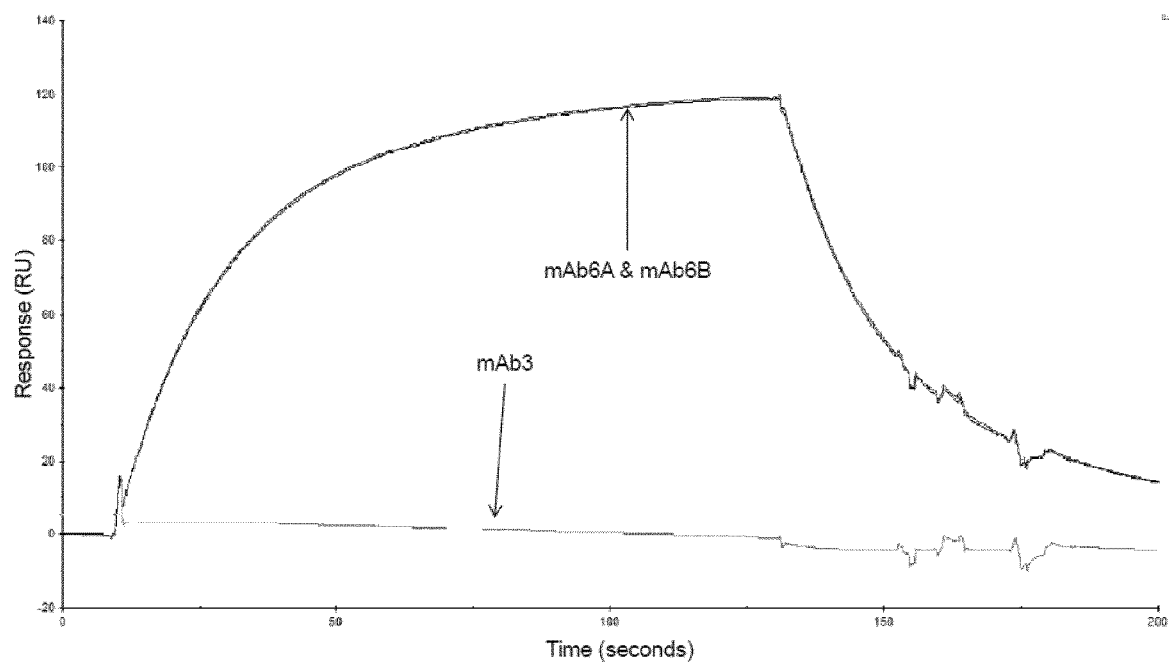

FIG. 5: Binding of PLBL2 to mAb3, mAb6A and mAb6B. Surface plasmon resonance sensograms of PLBL2 binding to mAb3 and mAb6 expressed in two different host cell expression systems. mAb6A was expressed using a CHO K1a host system, whilst mAb6B was expressed using a HEK293 host expression system. Results show that both IgG4 molecules (mAb6A and mAb6B) interact comparably with PLBL2 despite being generated in different cell lines. The IgG2 molecule (mAb3) meanwhile does not interact.

FIG. 6A-C: PLBL2 binding affinity to mAb3, mAb6A and mAb6B. Results of Bio Layer Interferometry (BLI) experiments on (A) mAb3, (B) mAb6A and (C) mAb6B showing the fitting of binding affinities of these molecules to PLBL2. $K_D$ results were calculated using a local fit with a 1:1 binding model. Note that affinity data could not be acquired for mAb3 as there was no interaction.

Figure 7:
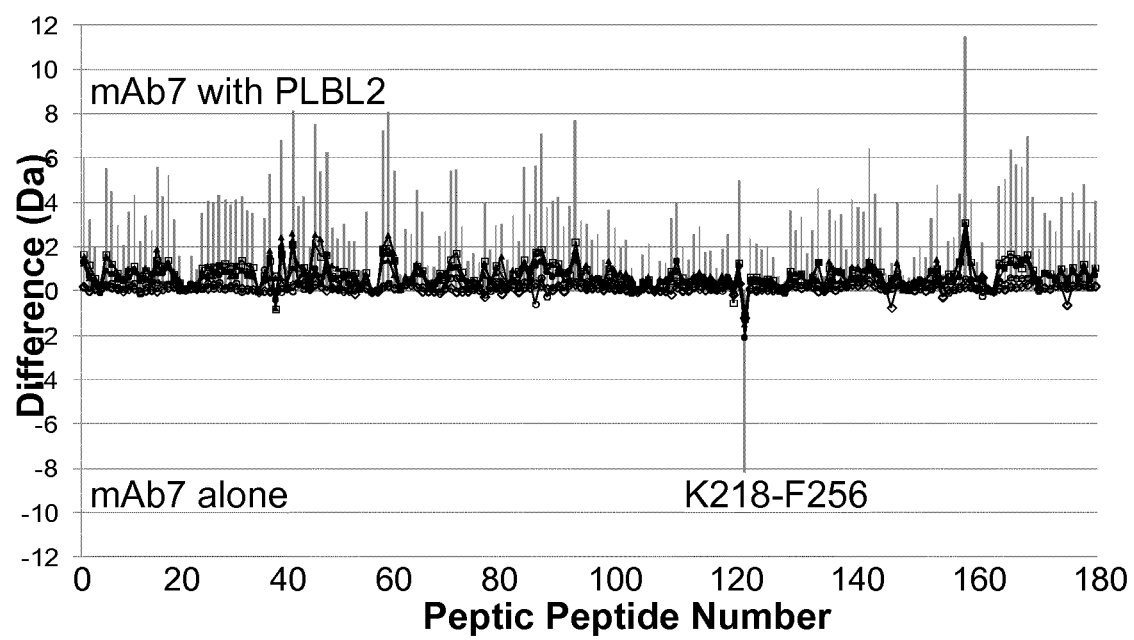

FIG. 7: HDX Differential Plot of mAb7 alone and PLBL2 Bound Samples. Deuterium labelling was measured at 0.5 min, 5 min, 60 min, 120 min, 180 min, and 240 min. Vertical sticks represent the total HDX differences of each peptide from six labeling time points. The sequence region with significant reduced solvent exposure is marked as K218-F256 (Heavy Chain).

FIG. 8: Sequence Alignment of different mAbs. The amino acid sequences of the lower CH1, Hinge and Upper CH2 domains of mAb1-7 were aligned against the amino acids in corresponding positions of a human germline IgG1, IgG2 and IgG4. The alignment was confined to the hinge region of the IgG4, which is the likely PLBL2 binding site based on experiment comparing the PLBL2 binding of different mAb molecules. Differences between the sequences are highlighted in grey. Amino acid residues of interest are those that are conserved in the IgG4 molecules, in which PLBL2 was observed to bind to, and not conserved (i.e. a different residue) in the other IgG subtypes, in which PLBL2 was observed to not bind to. 10 such amino acids were identified, which are outlined by a black box.

Figure 9:
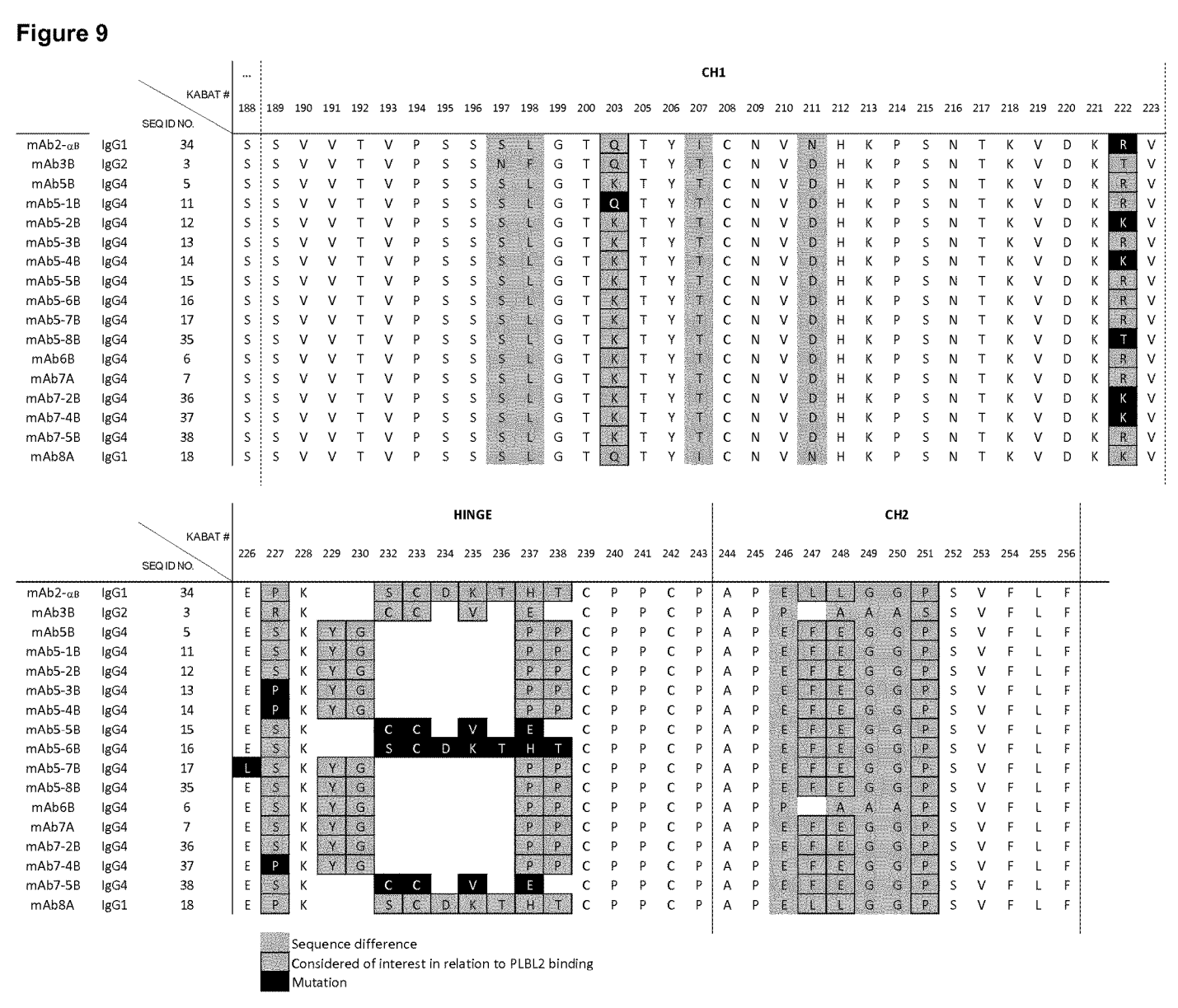

FIG. 9: Sequence Alignment of different mAbs via mutagenesis. A total of 7 different hinge modified IgG4 variants (mAb5-1B to 7B) were created via mutagenesis of a parent IgG4 (mAb5). This alignment compares the amino acid sequence of the IgG4 variants to that of the parent IgG4 as well as two other non-hinge modified IgG4s (mAb6 and mAb7), and IgG2 (mAb3) and an IgG1 (mAb8). The suffix "A" or "B" denotes whether the antibody was expressed via a CHO (A) or HEK (B) mammalian host cell. Differences in amino acid sequence are highlighted in grey. Outlined grey boxes then highlight the amino acid residues which were considered to play a role in influencing PLBL2 binding. Mutations of the hinge sequence in the IgG4 variants are highlighted in Black.

Figure 10:
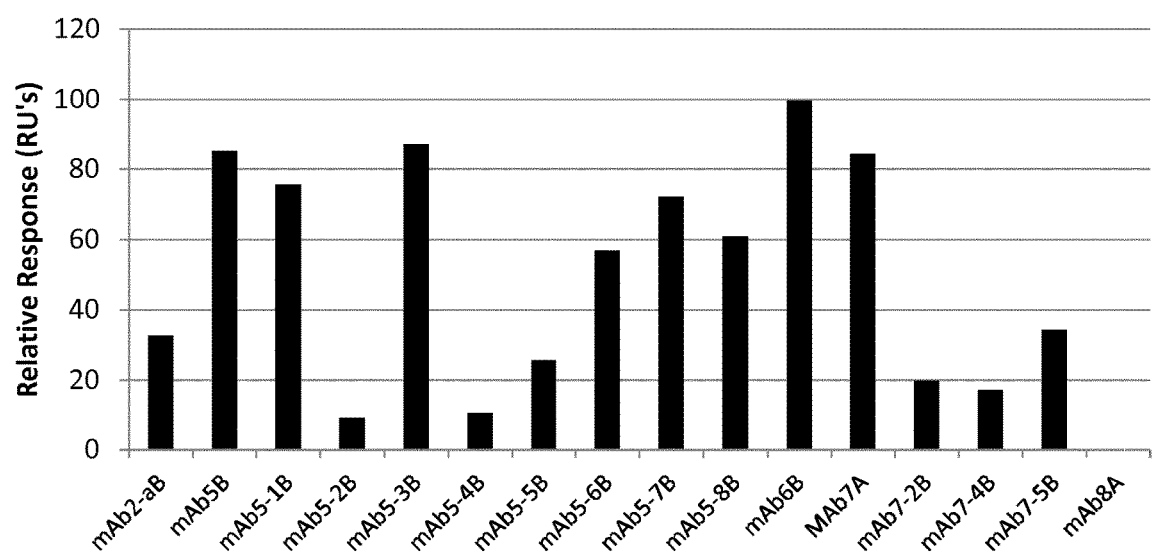

FIG. 10: Interaction of IgG2, IgG4 and Variant IgG4 molecules with PLBL2. Results of Surface Plasmon Resonance (SPR) experiments testing the binding of PLBL2 to hinge modified IgG4 variants (mAb5-1B to 7B) compared to the unmodified parent (mAb5B). Several other mAbs including an IgG1 (mAb8A), IgG2 (mAb3B) and IgG4s (mAb6B and mAb7A) were included in the analysis as further controls. The suffix "A" or "B" denotes whether the antibody was expressed via a CHO (A) or HEK (B) mammalian host cell.

DETAILED DESCRIPTION OF THE INVENTION

This present invention relates to antibodies which have a reduced interaction with process impurities such as HCPs, including PLBL2. It has been found that modification (e.g. by substitution, insertion, or deletion) of amino acids at residues at certain positions, results in a reduction in the ability of certain antibodies to bind HCPs such as PLBL2. This reduced propensity for interaction results in a decreased level of co-purification of a process impurity such as PLBL2, eliminating the need for specific purification strategies aimed at clearing this process related impurity. Indeed, for example, the levels of PLBL2 binding to IgG4 molecules incorporating these amino acid residue changes are in line with those in which PLBL2 co-purification is not found to be an issue. This in turn increases the efficiency of the manufacturing process, decreases associated costs, mitigates the need for excessive product testing and ultimately helps to ensure patient safety. In addition to this, lipases such as PLBL2 has been identified as a potential causative agent for the degradation of formulation excipients such as Polysorbate 80, which are necessary for the stabilisation of the product protein (recombinant antibody) in the final formulation. Reducing the binding of PLBL2 will serve to minimise the potential levels of this HCP in the final formulated drug, thereby maximising the shelf life of the product (recombinant antibody) which will further reduce costs and ensure safety.

Effector Function of IgG4

IgG4 shares more than 95% sequence homology in the heavy chain constant region with the IgG isotypes IgG1, IgG2 and IgG3. IgG4 has a low binding affinity to the activating Fc gamma receptors: FcγRIIa and FcγRIIIa, compared with IgG1. IgG4 has a weak to intermediate binding affinity to the high-affinity FcγRI, compared with IgG1. IgG4 maintains the binding affinity to the inhibitory FcγRIIb, similar to IgG1. IgG4 also binds to FcRn in a similar way to IgG1. IgG4 shows no or negligible binding to the C1q protein complex and is unable to activate the classical complement pathway, thereby having reduced CDC activity. IgG4 has reduced or no ADCC activity. This reduction in effector binding has led to the selection of the IgG4 heavy chain constant domain for use in recombinant antibodies where effector function is either unnecessary or is undesired.

The core IgG4 hinge comprises the sequence CPSC (SEQ ID NO: 19), whereas the core IgG1 hinge comprises CPPC (SEQ ID NO: 20), which is less susceptible to reduction. The S241 (Kabat) in IgG4 results in a more flexible hinge enabling the formation of an intrachain cyclized disulphide and leads to the appearance of 'half-antibodies', which contain non-covalently linked heavy chains from different antibodies, commonly known as IgG4 Fab arm exchange. The core hinge of IgG4 can be stabilised by modifying the S241 to proline (i.e. S241P), as in IgG1.

A number of therapeutic IgG4 antibodies have a hinge-engineered region including the S241P substitution. An IgG4-S241P single substitution is possible in the absence of the L248E variant, to retain normal FcγRI binding. The IgG4 L248E variant reduces the binding affinity of IgG4-PE to FcγRI versus IgG1 and has about 20 fold weaker affinity for FcγRI than IgG4 wild type.

IgG4 Sequence Modifications

The inventors have identified an unexpected connection between the conserved region of an IgG molecule, and the ability for said molecule to bind process impurities such as HCPs, including but not limited to PLBL2. Specifically, the inventors have identified key amino acid residues in the highly conserved hinge region and surrounding sequence of antibodies of the IgG4 subclass, which are responsible for causing the binding of these antibodies to HCPs, such as PLBL2. When these amino acid residues are modified the resultant modified IgG4 molecule shows a reduced ability to bind HCPs such as PLBL2, compared to a parental IgG4 molecule without the aforementioned modification(s), whilst maintaining the same IgG4 effector functions (e.g. FcRn receptor binding behaviour of an IgG4 molecule), without said modification(s). Furthermore, the modified IgG4 molecule at least maintains (or enhances) the biophysical properties such as stability, shear behaviour, of an IgG4 without said modification(s).

Therefore, according to a first aspect of the invention, there is provided a variant IgG4 antibody which has been modified in the heavy chain constant region at any one or a combination of amino acids in the region between Kabat residues 203 and 256, wherein the variant IgG4 antibody has a reduced level of binding to host cell protein (HCP), compared to an unmodified IgG4 antibody.

In one embodiment, the one or a combination of amino acids are between Kabat residues 203 and 243. In a further embodiment, the one or a combination of amino acids are between Kabat residues 222 and 243. In an alternative embodiment, the one or a combination of amino acids are between Kabat residues 222 and 256.

In one embodiment, the one or a combination of amino acids are selected from the group consisting of: (i) one or more amino acids of the hinge region between Kabat residues 226 and 243; and/or (ii) Kabat residue 203; and/or (iii) Kabat residue 222.

In one embodiment, the unmodified IgG4 antibody has a hinge region sequence of ESKYGPPCPSCP (SEQ ID NO: 21) or ESKYGPPCPPCP (SEQ ID NO: 22) (i.e. Kabat positions 226-243).

In one embodiment, the hinge region is between Kabat residues 203 and 256. In one embodiment, the hinge region is between Kabat residues 226 and 243. In a further embodiment, the hinge region is between Kabat residues 226 and 238. In an alternative embodiment, the hinge region is between Kabat residues 234 and 250.

In one embodiment, the variant IgG4 antibody comprises the sequence CPPC (SEQ ID NO: 20) (Kabat residues 239 to 242). This is known as the "core hinge". In an alternative embodiment, the variant IgG4 antibody comprises the sequence CPSC (SEQ ID NO: 19) (Kabat residues 239 to 242).

In one embodiment, the modification comprises a deletion of any one or a combination of amino acids in the region between Kabat residues 203 and 256.

In one embodiment, the modification comprises an insertion of one or more amino acids in the region between Kabat residues 203 and 256.

In one embodiment, the modification comprises a substitution of one or more amino acids in the region between Kabat residues 203 and 256.

The key IgG4 amino acid residues, present in or nearby the hinge region of the heavy chain are: serine at position 197 (S197), Leucine at position 198 (L198), lysine at position 203 (K203), threonine at position 207 (T207), aspartate at position 211 (D211), arginine at position 222 (R222), glutamate at position 226 (E226), serine at position 227 (S227), tyrosine at position 229 (Y229), glycine at position 230 (G230), proline at position 237 (P237), proline at position 238 (P238), glutamate at position 246 (E246), phenylalanine at position 247 (F247), glycine at position 249 (G249), glycine at position 250 (G250), and proline at position 251 (P251). The sequences of interest are shown in FIGS. 8 and 9.

Key IgG4 amino acid residues are: lysine at position 203 (K203), arginine at position 222 (R222), glutamate at position 226 (E226), serine at position 227 (S227), tyrosine at position 229 (Y229), glycine at position 230 (G230), proline at position 237 (P237) and proline at position 238 (P238). Modification of the IgG4 hinge region may comprise making one or more amino acid substitutions around these positions, resulting in a modified IgG4 molecule with a reduced ability to bind HCPs, such as PLBL2.

In addition, modification of the IgG4 hinge region may comprise removing the tyrosine at position 229 (Y229) and/or the glycine at position 230 (G230), and in certain embodiments, these eliminations are combined with at least one amino acid substitution or further elimination at one of the previously listed positions, resulting in a variant IgG4 antibody with a reduced ability to bind HCPs such as PLBL2, compared to the parental IgG4 antibody.

In another embodiment, modification of the IgG4 hinge region may comprise removing the tyrosine at position 229 (Y229) and/or the glycine at position 230 (G230), combined with at least one amino acid substitution or further elimination of the proline residues at positions 237 and 238 (P237 and P238), resulting in a variant IgG4 antibody with a reduced ability to bind HCPs such as PLBL2, compared to the parental IgG4 antibody. In one embodiment, the modification comprises replacement of YGPP (SEQ ID NO: 23) (Kabat residues 229 to 238) with SCDKTHT (SEQ ID NO: 24), or COVE (SEQ ID NO: 25).

In one embodiment, the modification comprises a substitution to the equivalent amino acid sequence in an IgG1, IgG2, and/or IgG3 antibody germline sequence. In a further embodiment, the IgG1, IgG2, and/or IgG3 antibody germline sequence is human. IgG antibody germline sequences are well known in the art. For example, the IgG1 germline sequence between positions 203 and 256 inclusive, is shown in FIG. 8 and as SEQ ID NO: 8. The IgG2 germline sequence between positions 203 and 256 inclusive, is shown in FIG. 8 and as SEQ ID NO: 9.

In one embodiment, modification of the IgG4 hinge region comprises substituting one of more of the following key amino acid residues: lysine at position 203 (K203), arginine at position 222 (R222), glutamate at position 226 (E226), serine at position 227 (S227), tyrosine at position 229 (Y229), glycine at position 230 (G230), proline at position (P237) and proline at position 238 (P238), with an amino acid residue at the corresponding position from the germline sequence of a human antibody of an alternate isotype. The alternate isotype could be an IgG1, an IgG2 or an IgG3. In such embodiments, in which more than one substitution is made, the substitutions do not necessarily need to be selected based on only one alternate IgG isotype, but may instead be a combination of residues from more than one alternate human antibody isotype. The variant IgG4 of such an embodiment could therefore foreseeably be comprised of amino acid residues, in these key positions, from an IgG1 germline sequence and an IgG2 germline sequence, or an IgG1 germline sequence and an IgG3 germline sequence, or an IgG2 germline sequence and an IgG3 germline sequence, or an IgG1, IgG2 and IgG3 germline sequence.

In embodiments in which the germline sequence of an alternate isotype does not contain an amino acid at a position corresponding to the key aforementioned residues in the IgG4 germline sequence, then the variant IgG4 of such an embodiment has the amino acid residue or residues at said position(s), eliminated from the protein sequence.

In one embodiment, the modification comprises any one or a combination of:

(i) substitution of one or more amino acids comprising K203 to R, E, or Q; R222 to T, K, or Q; E226 to L or I; S227 to R, P, A, N, or T; Y229 to S, C, F, W, or H; G230 to C, A, N, or S; P237 to H, E, D, or V; and/or P238 to T, K, or E; and/or (ii) replacement of ESKYGPP (SEQ ID NO: 26) (Kabat residues 226 to 238) with EPKSCDKTHT (SEQ ID NO: 27), or ERKYGPP (SEQ ID NO: 28), or ERKCCVE (SEQ ID NO: 29), or ELKTPLGDTTHT (SEQ ID NO: 30); and/or (iii) replacement of YGPP (SEQ ID NO: 23) (Kabat residues 229 to 238) with SCDKTHT (SEQ ID NO: 24), or COVE (SEQ ID NO: 25). These modifications are summarised in Table 1.

In one embodiment, the variant IgG4 molecule has the lysine at position 203 in the germline sequence, substituted with glutamine (K203Q).

In one embodiment, the variant IgG4 molecule has the arginine at position 222 in the germline sequence, substituted with a residue selected from the group consisting of: lysine, threonine, alanine, arginine, asparagine, aspartate, cysteine, glutamate, glutamine, glycine, histidine, isoleucine, leucine, methionine, phenylalanine, proline, serine, tryptophan, tyrosine and valine. In a further embodiment, the variant IgG4 molecule has the arginine at position 222 in the germline sequence, substituted with a residue selected from the group consisting of: lysine and threonine. In a yet further embodiment, the variant IgG4 molecule has the arginine at position 222 in the germline sequence, substituted with threonine (R222T). In a yet further embodiment, the variant IgG4 molecule has the arginine at position 222 in the germline sequence, substituted with lysine (R222K). As shown in the Examples described herein, modifications at this position showed the greatest reduction in PLBL2 binding.

In one embodiment, the variant IgG4 molecule has the glutamate at position 226 in the germline sequence, substituted with a residue selected from the group consisting of: isoleucine and leucine. For example the substitution is E226L.

In one embodiment, the variant IgG4 molecule has the serine at position 227, substituted with a residue selected from the group consisting of: proline and arginine. For example the substitution is S227P.

In one embodiment, the variant IgG4 molecule does not contain the tyrosine which is at position 229 in the germline human IgG4 sequence.

In one embodiment, the variant IgG4 molecule does not contain the glycine which is at position 230 in the germline human IgG4 sequence.

In one embodiment, the variant IgG4 molecule does not contain the proline which is at position 237 in the germline human IgG4 sequence.

In one embodiment, the variant IgG4 molecule does not contain the proline which is at position 238 in the germline human IgG4 sequence.

In one embodiment, the variant IgG4 molecule has the tyrosine at position 229, substituted with a residue selected from the group consisting of: lysine, asparagine, threonine, arginine, methionine, isoleucine, glutamine, histidine, proline, glutamate, aspartate, alanine, glycine, valine, tyrosine, serine, tryptophan, cysteine, leucine and phenylalanine.

In one embodiment, the variant IgG4 molecule has the glycine at position 230, substituted with a residue selected from the group consisting of: lysine, asparagine, threonine, arginine, methionine, isoleucine, glutamine, histidine, proline, glutamate, aspartate, alanine, glycine, valine, tyrosine, serine, tryptophan, cysteine, leucine and phenylalanine.

In one embodiment, the variant IgG4 molecule has the proline at position 237, substituted with a residue selected from the group consisting of: lysine, asparagine, threonine, arginine, methionine, isoleucine, glutamine, histidine, proline, glutamate, aspartate, alanine, glycine, valine, tyrosine, serine, tryptophan, cysteine, leucine and phenylalanine.

In one embodiment, the variant IgG4 molecule has the proline at position 238, substituted with a residue selected from the group consisting of: lysine, asparagine, threonine, arginine, methionine, isoleucine, glutamine, histidine, proline, glutamate, aspartate, alanine, glycine, valine, tyrosine, serine, tryptophan, cysteine, leucine and phenylalanine.

In one embodiment, the variant IgG4 molecule does not contain tyrosine at position 229, glycine at position 230, proline at position 237 and proline at position 238 and instead contains the following peptide sequence: SCDKTHT (SEQ ID NO: 24). In an alternative embodiment, the variant IgG4 molecule does not contain tyrosine at position 229, glycine at position 230, proline at position 237 and proline at position 238 and instead contains the following peptide sequence: COVE (SEQ ID NO: 25). For example, the variant IgG4 comprises a deletion of Kabat 229-238 YGPP (SEQ ID NO: 23), and an insertion of COVE (SEQ ID NO: 25). For example, the variant IgG4 comprises a replacement of Kabat 229-238 YGPP (SEQ ID NO: 23), with COVE (SEQ ID NO: 25). Examples described herein, modifications at these positions showed the greatest reduction in PLBL2 binding.

In one embodiment, the variant IgG4 molecule has the phenylalanine at position 247, substituted with leucine.

In one embodiment, the modification comprises replacement of EFLGGP (SEQ ID NO: 31) (Kabat residues 246 to 251) with PAAAS (SEQ ID NO: 32) or PAAAP (SEQ ID NO:33).

Examples of possible amino acid modifications, (e.g. substitutions, and/or insertions, and/or deletions) at particular Kabat residues, which are summarised in Table 1, may be made to an IgG4 antibody to create a modified IgG4 antibody with a reduced ability to bind HCPs such as PLBL2. These modifications can be made at any one or more (i.e. a combination) of amino acids.

In another embodiment, the substitution to an equivalent amino acid sequence in the IgG1, IgG2, and/or IgG3 antibody germline sequence, involves a human antibody germline sequence.

In one embodiment, the modification is made to both heavy chains of the variant IgG4 molecule. In an alternative embodiment, the modification is made to only one of the heavy chains of the variant IgG4 molecule.

In one embodiment, no further modifications are made in the heavy chain constant region in comparison to the unmodified IgG4 antibody.

In one embodiment, no modifications are made to amino acid residues required for IgG4 effector function. For example, wild-type IgG4 F247 (Kabat) (EU F234), is important for attenuated ADCC and CDC activity. Furthermore, modified E248 (Kabat) can dampen effector functions, specifically reducing binding to FcγRI.

In one embodiment, the variant IgG4 antibody comprises a further substitution of S241 to P and/or L248 to E. In one embodiment, the variant IgG4 antibody comprises a further substitution of S241 to P. This modification helps to improve

TABLE 1

Examples of amino acid modifications within IgG4 heavy chain

| Kabat Heavy Chain Position | Germline IgG4 Amino Acid | Modification(s) to Reduce HCP Binding |
|---|---|---|
| 197 | S | Substitution to N |
| 198 | L | Substitution to F |
| 203 | K | Substitution to Q, E or R |
| 207 | T | Substitution to I |
| 211 | D | Substitution to N |
| 222 | R | Substitution to K, T or Q |
| 226 | E | Substitution to I or L |
| 227 | S | Substitution to R, P, A, N or T |
| 229 | Y | Substitution to S, C, F, W or H |
| 230 | G | Substitution to C, A, N or S |
| 237 | P | Substitution to H, E, D or V |
| 238 | P | Substitution to T, K or E |
| 229, 230, 237 & 238 | YGPP (SEQ ID NO: 23) | Replacement with SCDKTHT (SEQ ID NO: 24) or CCVE (SEQ ID NO: 25) |
| 226-230, 237 & 238 | ESKYGPP (SEQ ID NO: 26) | Replacement with EPKSCDKTHT, ERKYGPP, ERKCCVE or ELKTPLGDTTHT (SEQ ID NOs: 27, 28, 29 and 30, respectively) |
| 246 | E | Substitution to P |
| 247 | F | Substitution to L |
| 246-251 | EFLGGP (SEQ ID NO: 31) | Replacement with PAAAS (SEQ ID NO: 32) or PAAAP (SEQ ID NO: 33) |
| 248 | E | Substitution to L or A |
| 251 | P | Substitution to S |

In one embodiment, the variant IgG4 antibody is human or humanised.

the stability of the IgG4 molecule. In one embodiment, the variant IgG4 antibody comprises a further substitution of EFLGGP sequence (SEQ ID NO: 31) (Kabat residues 246-251) with the sequence PAAAP (SEQ ID NO: 33).

According to a further aspect of the invention, there is provided a nucleic acid construct encoding the variant IgG4 antibody as defined herein.

The nucleic acid construct can be transfected into a host cell line. Therefore, according to a further aspect of the invention, there is provided a cell line encoding the variant IgG4 antibody as defined herein.

Further Sequence Modifications

According to a further aspect of the invention, there is provided a variant IgG antibody which has been modified in the heavy chain constant region at any one or a combination of amino acids in the region between Kabat residues 203 and 256, wherein the variant IgG antibody has a reduced level of binding to host cell protein (HCP), compared to an unmodified IgG antibody. For example, the variant IgG antibody has been modified at 1 to 25 amino acids in the heavy chain constant region between Kabat residues 203 and 256. For example, the variant IgG antibody has been modified at one, two, three, four, five, six, seven, eight, nine, ten, eleven, twelve, thirteen, fourteen, fifteen, sixteen, seventeen, eighteen, nineteen, twenty, twenty-one, twenty-two, or twenty-three amino acids in the heavy chain constant region between Kabat residues 203 and 256. For example, the variant IgG antibody has been modified at any one or a combination of Kabat positions 197, 198, 203, 207, 211, 222, 226, 227, 229, 230, 232, 233, 234, 235, 236, 237, 238, 246, 247, 248, 249, 250, or 251 in the heavy chain constant region. For example, the variant IgG antibody has been modified at any one or a combination of Kabat positions 203, 222, 226, 227, 229, 230, 232, 233, 234, 235, 236, 237, 238, 247, 248, or 251 in the heavy chain constant region.

Host Cell Proteins

Host cell proteins, or "HCP", refers to proteins, not related to the protein of interest (i.e. the recombinant protein/variant IgG4), produced by the host cell during cell culture or fermentation, including intracellular and/or secreted proteins. An example of a host cell protein is a protease, which can cause damage to the protein of interest if still present during and after purification. For example, if a protease remains in the sample comprising the protein of interest, it can create product-related substances or impurities which were not originally present. The presence of proteases can cause decay of the protein of interest over time during the purification process, and/or in the final formulation.

In one embodiment, the host cell proteins are produced/derived from a mammalian cell or a bacterial cell. In a further embodiment, the mammalian cell is selected from a human or rodent (such as a hamster or mouse) cell.

In certain embodiments the host cell used to express the antibody is selected from the group consisting of selected from the group consisting of CHO cells, NS0 cells, Sp2/0 cells, COS cells, K562 cells, BHK cells, PER.C6 cells, and HEK cells (i.e., the host cell proteins are derived from these host cells). Alternatively, the host cell may be a bacterial cell selected from the group consisting of *E. coli* (for example, W3110, BL21), *B. subtilis* and/or other suitable bacteria; eukaryotic cells, such as fungal or yeast cells (e.g., *Pichia pastoris, Aspergillus* sp., *Saccharomyces cerevisiae, Schizosaccharomyces pombe, Neurospora crassa*). For example, the host cell is a CHO cell. Alternatively, the host cell is a HEK cell.

In one embodiment, the host cell protein is putative phospholipase B-Like 2 (PLBL2). PLBL2 is also known as phospholipase B domain containing protein 2 (PLBD2).

Reducing the binding of IgG4 molecules to HCPs such as PLBL2 results in a concomitant decrease in the level of co-purification of these process related impurities with the product IgG4. This in turn eliminates the need for specific purification strategies, such as stringent wash conditions during pack bed column chromatography, to clear HCPs from the drug product. Doing so increases the efficiency of the manufacturing process, decreases the associated costs and mitigates the need for excessive product testing using potentially bespoke immunoassays. Ultimately, these modifications serve to potentially mitigate the risk of HCPs such as PLBL2 being present in the final drug product and as a result minimises the potential for them to cause an immunogenic response in patients.

The reduced ability of these modified IgG4 molecules to bind HCPs, such as PLBL2, can be quantified based on methods provided in the Examples.

There are several ways in which the reduced level of binding to host cell protein can be measured. For example, a reduced level of binding can be assessed by simply measuring the amount of host cell protein present in solution with the antibody once it has been purified, e.g. by affinity chromatography (a reduced amount compared to an unmodified IgG4 is indicative of reduced host cell protein binding). In one embodiment, the IgG4 antibody has reduced binding affinity and/or activity to host cell protein in comparison to the unmodified IgG4 antibody.

In one embodiment, the variant IgG4 antibody has at least a 10% reduction in binding activity compared to an unmodified IgG4 antibody, such as at least 15%, 20%, 25%, 30%, 35%, 40%, 45%, 50%, 55%, 60%, 65%, 70%, 75%, 80%, 85%, 90%, 95%, 98%, 99% reduction in binding activity.

In one embodiment, the variant IgG4 antibody has at least a 10-fold reduction in binding affinity compared to an unmodified IgG4 antibody, such as at least 10%, 15%, 20%, 25%, 30%, 35%, 40%, 45%, 50%, 55%, 60%, 65%, 70%, 75%, 80%, 85%, 90%, 95%, 98%, 99% reduction in binding affinity.

Compositions Comprising Antibody Variants

According to a further aspect of the invention, there is provided a composition comprising the variant IgG4 antibody as defined herein.

The compositions of the present invention may be formulated with pharmaceutically acceptable carriers or diluents as well as any other known adjuvants and excipients in accordance with conventional techniques. The pharmaceutically acceptable carriers or diluents, as well as any other known adjuvants and excipients, should be suitable for the chosen compound of the present invention and the chosen mode of administration.

In one embodiment, the variant IgG4 is at a concentration of at least 10 mg/mL, for example at least 20 mg/mL, 25 mg/mL, 30 mg/mL, 35 mg/mL, 40 mg/mL, 45 mg/mL, 50 mg/mL, 55 mg/mL, 60 mg/mL, 65 mg/mL, 70 mg/mL, 75 mg/mL, 80 mg/mL, 85 mg/mL, 90 mg/mL or 95 mg/mL or 100 mg/mL.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required.

In one embodiment, the concentration of putative phospholipase B-Like 2 (PLBL2) in the composition is less than 500 ppm, for example less than 400 ppm, 300 ppm, 200 ppm, 100 ppm, 90 ppm, 80 ppm, 70 ppm, 60 ppm, 50 ppm, 40 ppm, 30 ppm, 20 ppm or 10 ppm.

In one embodiment, the concentration of putative phospholipase B-Like 2 (PLBL2) in the composition is less than about 200 ng of PLBL2/mg of product (i.e. ng/mg); less than about 150 ng/mg; less than about 100 ng/mg; or less than about 50 ng/mg.

In one embodiment, the composition additionally comprises a buffer and/or a fatty acid ester. In a further embodiment, the fatty acid ester is Polysorbate 20 or Polysorbate 80.

As mentioned hereinbefore, PLBL2 has been identified as a potential causative agent for the degradation of formulation excipients such as polysorbates, which are necessary for the stabilisation of the product protein in the final formulation. Therefore, reducing the binding of PLBL2 will in turn minimise the level of PLBL2 in the final formulated drug, thereby maximising the shelf life of the product. Therefore, according to a further aspect of the invention, there is provided a composition with an extended/improved shelf life comprising the variant IgG4 antibody as defined herein.

Furthermore, according to a further aspect of the invention, there is provided a method of extending the shelf life of an antibody composition comprising producing an IgG4 antibody with reduced binding to PLBL2 by modifying the antibody sequence in the heavy chain constant region at any one or a combination of amino acids in the region between Kabat residues 203 and 256.

Uses of Antibody Variants

According to a further aspect of the invention, there is provided the variant IgG4 antibody as defined herein for use in therapy. It will be understood by a person skilled in the art that the present invention could be applied to a variety of IgG4 antibodies directed to different targets, therefore said IgG4 variants can be used to treat a range of diseases.

The antibodies described herein may also be used in methods of treatment. Treatment can be therapeutic, prophylactic or preventative. Treatment encompasses alleviation, reduction, or prevention of at least one aspect or symptom of a disease and encompasses prevention or cure of the diseases described herein.

The antibodies described herein may be used in an effective amount for therapeutic, prophylactic or preventative treatment. A therapeutically effective amount of the antibody described herein is an amount effective to ameliorate or reduce one or more symptoms of, or to prevent or cure, the disease.

Methods of Preparing Antibody Variants

Provided herein are antibody variants and methods to produce said antibody variants which have been modified via amino acid sequence changes in order to reduce the level of process impurity binding. These modifications have the beneficial effect of reducing the amount of process impurity present in the resulting medicinal product.

Therefore, according to a further aspect of the invention, there is provided a method of modifying an IgG antibody to reduce binding to a process impurity, comprising the steps of:
a) identifying at least one amino acid involved in the binding of the process impurity; and
b) creating a variant of the IgG antibody by substituting the amino acid identified as being involved in the binding with the process impurity with a different amino acid.

According to a further aspect of the invention, there is provided a method for creating a variant of an IgG antibody with reduced binding to a process impurity compared to the unmodified IgG antibody, comprising the steps of:
a) identifying at least one amino acid, involved in the binding of the process impurity; and
b) creating a variant of the IgG antibody by substituting the amino acid identified as being involved in the binding with the process impurity with a different amino acid.

In one embodiment, the amino acid involved in the binding of the process impurity is identified through the use of a method or combination of methods which may be used to study protein-protein interactions. In one embodiment, the method for studying protein-protein interactions is selected from the group consisting of: hydrogen deuterium exchange mass spectrometry (HDX-MS), crystallography, Yeast 2-Hybrid screening, in silico 3D structure modelling or any combination thereof. Such embodiments, may require combining the outputs of a number of these methods, and through application of appropriate scientific reasoning the identity of the amino acid or amino acids involved in binding of the process impurity may be deduced.

In one embodiment, the amino acid identified as being involved in the binding of the process impurity is present in the constant region. In a further embodiment, the amino acid identified as being involved in the binding of the process impurity is present in the heavy chain constant region.

Sequence alignments of IgG isotypes which do interact with the process impurity against isotypes which do not, in the region determined by protein-protein interaction methods (e.g. HDX-MS) allow the amino acid(s) involved in the binding of the process impurity to be identified. Conservative germline to germline substitutions, from an IgG isotype which does not bind with the process impurity into the IgG which does, will then allow a variant to be created which does not bind to the process impurity. Therefore, in one embodiment, the amino acid identified as being involved in the binding with a process impurity is substituted with the equivalent amino acid from an alternate IgG antibody germline sequence.

In one embodiment, the amino acid identified as being involved in the binding with a process impurity is modified through conservative, same species, immunoglobulin germline-to-germline amino acid changes in the conserved region of the antibody sequence.

Therefore, provided herein is a method of producing an IgG4 antibody with reduced binding to host cell protein (HCP) comprising modifying the antibody sequence in the heavy chain constant region at any one or a combination of amino acids in the region between Kabat residues 203 and 256. In one example, the host cell protein is putative phospholipase B-Like 2 (PLBL2). The method may additionally comprise purifying the IgG4 antibody using an affinity chromatographic technique. The method may additionally comprise further purifying the IgG4 antibody using at least one other orthogonal chromatographic technique. In one example, the orthogonal chromatographic technique is ion exchange chromatography.

The present invention therefore provides antibody variants which are produced by site-directed mutagenesis, rather than being purified by more classical chromatography methods, in order to reduce the levels of an associated process impurity. According to a further aspect of the invention, there is provided an IgG antibody obtained by the methods defined herein.

In one embodiment, the IgG antibody is an IgG4 antibody. Therefore, in this embodiment, the amino acid identified as being involved in the binding with a process impurity is substituted with the equivalent amino acid from an IgG1, IgG2, and/or IgG3 antibody germline sequence.

Methods of Preparing IgG4 Antibody Variants

According to a further aspect of the invention, there is provided a method of producing an IgG4 antibody with reduced binding to host cell protein (HCP) comprising modifying the antibody sequence in the heavy chain constant region at any one or a combination of amino acids in the region between Kabat residues 203 and 256.

Methods of producing antibodies are well known to a person skilled in the art. For example, the method may comprise preparing a suspension culture of recombinant host cells transformed or transfected with a recombinant polynucleotide encoding for said IgG4 antibody; and culturing said host cell culture under conditions permitting the expression of said IgG4 antibody. The method may additionally comprise purifying the IgG4 antibody using an affinity chromatographic technique. The method may additionally comprise further purifying the IgG4 antibody using at least one other orthogonal chromatographic technique. In one example, the orthogonal chromatographic technique is ion exchange chromatography.

In one embodiment, the method additionally comprises purifying the IgG4 antibody (e.g. following culturing), for example using an affinity chromatographic technique. In a further embodiment, the affinity chromatographic technique is superantigen affinity chromatography. In one embodiment, the superantigen is selected from Protein A, Protein G and Protein L. Therefore, in a further embodiment, the superantigen affinity chromatography is selected from Protein A affinity chromatography, Protein G affinity chromatography and Protein L affinity chromatography.

In one embodiment, the method additionally comprises further purifying the IgG4 antibody using at least one other chromatographic technique, such as ion exchange chromatography. In one embodiment, the one or more further chromatography steps are selected from the group consisting of: anion exchange chromatography, cation exchange chromatography and mixed-mode chromatography, in particular anion exchange chromatography. In one embodiment, the at least one other chromatographic technique does not include hydrophobic interaction chromatography.

The method may also include filtration steps such as depth filtration (for removal of cells and cellular debris) and nanofiltration (for removal of viruses). The purifying step can also be taken to include any virus inactivation steps for material generated using mammalian expression systems.

According to a further aspect of the invention, there is provided a method of producing the variant IgG4 antibody as defined herein, said method comprising expressing a nucleic acid construct encoding said antibody in a host cell and optionally purifying said antibody.

According to a further aspect of the invention, there is provided an IgG4 antibody obtained by the methods defined herein.

DEFINITIONS

Unless defined otherwise, all technical and scientific terms used herein have the same meaning as commonly understood by one of ordinary skill in the art (e.g. in cell culture, molecular genetics, nucleic acid chemistry, hybridization techniques, protein purification and biochemistry). Standard techniques are used for molecular, genetic and biochemical methods and chemical methods.

As used herein, the term "antibody" refers to all immunoglobulins or IgGs (such as IgG1, IgG2, IgG3 or IgG4), IgM, IgA, IgD or IgE antibodies whether derived from any species naturally producing an antibody, or created by recombinant DNA technology; whether isolated from serum, B-cells, hybridomas, transfectomas, yeast or bacteria. The antibody may be monoclonal, recombinant, polyclonal, chimeric (for example, from different sources (e.g. a human/mouse chimeric antibody) or different antibody types (e.g. an IgG2/4 antibody)), human, humanised, multispecific (including bispecific), or a heteroconjugate antibody. The term also includes a single variable domain (e.g., VH, VHH, VL), a domain antibody (dAb®), antigen binding fragments, immunologically effective fragments, Fab, F(ab')2, Fv, disulphide linked Fv, single chain Fv, closed conformation multispecific antibody, disulphide-linked scFv, diabodies, TANDABS™, etc. In one embodiment, the antibody is an IgG4. In another embodiment, the antibody is a recombinant IgG4. In another embodiment, the antibody is a variant IgG4. In another embodiment, the antibody is a recombinant variant IgG4.

As used herein, the term "CDRs" are defined as the complementarity determining region amino acid sequences of an antibody which are the hypervariable regions of immunoglobulin heavy and light chains. There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate). The structure and protein folding of the antibody may mean that other residues are considered part of the antigen binding region and would be understood to be so by a skilled person.

As used herein the term "domain" refers to a folded protein structure which has tertiary structure independent of the rest of the protein. Generally, domains are responsible for discrete functional properties of proteins and in many cases may be added, removed or transferred to other proteins without loss of function of the remainder of the protein and/or of the domain.

The antibody is the protein product, i.e. the protein of interest. For example, the protein product is a variant IgG4. For example, the protein product is a recombinant IgG4. For example, the protein product is a recombinant variant IgG4.

As used herein, the terms "hinge region" and/or "hinge sequence" refer to what is conventionally known as the hinge region of an antibody, that is the domain of an IgG molecule covering amino acids in positions 226 to 243 inclusive, of the molecule protein sequence wherein the amino acid number is according to Kabat numbering, or positions 216-230 inclusive, according to EU numbering. These regions can also be referred to as the "genetic hinge". In addition to this, the terms "hinge region" and "hinge sequence" as used herein can be taken to also include amino acids in positions 203 to 223 inclusive, of the molecule protein sequence wherein the amino acid number is according to Kabat numbering, or position 196 to 215 inclusive according to EU numbering. Furthermore the terms "hinge region" and "hinge sequence" as used herein can be taken to include amino acids in positions 244 to 256 inclusive, of the molecule protein sequence wherein the amino acid number is according to Kabat numbering, or position 231 to 243 inclusive according to EU numbering.

Alternatively, the "structural hinge" has been defined as Kabat positions 234-250 (or EU positions 221-237), based on a hinge beginning at the residue after the H/L chain disulphide, and ending at the residue preceding the Fc domain.

The hinge can be divided structurally into an upper hinge (Kabat positions 234-238; or EU positions 221-225) which is the end of the Fab domain to the first interheavy disulphide formed by a one helix turn; and a low hinge (Kabat positions 243-250 or EU positions 230-237) from the last disulphide to the beginning of the Fc domain. The middle or core hinge is the "CPPC" (SEQ ID NO: 20) motif in human IgG1 (Kabat positions 239-242 or EU positions 226-229) which comprises two parallel polyproline double helices linked by disulphide bridges.

It should be noted that most numbering in the art is based on human IgG1 and will vary in particular hinge sequences due to indels. For example, the "YGPP" (SEQ ID NO: 23) motif next to the core hinge for IgG4 is equivalent to the "SCDKTHT" (SEQ ID NO: 24) motif in IgG1, hence why "YGPP" (SEQ ID NO: 23) of IgG4 is positions 229, 230, 237 and 238, respectively, rather than simply positions 229 to 232.

As used herein, the term "hinge modified" in the context of describing an antibody molecule, refers to any antibody, in which the amino acid residues between positions 203 to 256 inclusive of the protein sequence has been changed from that of the sequence of the unmodified and/or parent antibody. These changes may involve either substitution of the residue or residues for an alternate amino acid, or substitution of entire peptides sequences for alternate sequences. Changes may also involve elimination of an amino acid, or peptide sequence from the protein.

As used herein, the term "unmodified" refers to the antibody prior to the modification which reduces binding to process impurities. This may include an antibody in its natural, germline format. It may also include antibodies which have already been modified to improve properties other than reducing host cell protein binding, such as the substitution S241P (i.e. resulting in the sequence CPPC [SEQ ID NO: 20] at Kabat residues 239 to 242) which is used in many IgG4 antibodies to improve stability. Therefore, in one embodiment, the unmodified antibody comprises the substitution S241P. It may also include antibodies which have already been modified with the substitution L248E which is used in many IgG4 antibodies to improve effector function. Therefore, in one embodiment, the unmodified antibody comprises the substitution L248E.

The term "modified" is used herein to describe any one or a combination of substitution, and/or deletion, and/or insertion of one or a combination of amino acids in the region between Kabat residues 203 and 256 of the heavy chain constant region. For example, the modification may comprise one or more amino acid substitutions, and/or one or more amino acid insertions, and/or one or more amino acid deletions. The terms "deletion", "removal", "replacement", "elimination", are used herein interchangeably.

For example, the variant IgG antibody has been modified at 1 to 25 amino acids in the heavy chain constant region between Kabat residues 203 and 256. For example, the variant IgG antibody has been modified at one, two, three, four, five, six, seven, eight, nine, ten, eleven, twelve, thirteen, fourteen, fifteen, sixteen, seventeen, eighteen, nineteen, twenty, twenty-one, twenty-two, or twenty-three amino acids in the heavy chain constant region between Kabat residues 203 and 256. For example, the variant IgG antibody has been modified at any one or a combination of Kabat positions 197, 198, 203, 207, 211, 222, 226, 227, 229, 230, 232, 233, 234, 235, 236, 237, 238, 246, 247, 248, 249, 250, or 251 in the heavy chain constant region. For example, the variant IgG antibody has been modified at any one or a combination of Kabat positions 203, 222, 226, 227, 229, 230, 232, 233, 234, 235, 236, 237, 238, 247, 248, or 251 in the heavy chain constant region.

As used herein, the term "host cell" refers to any organism, both prokaryotic and eukaryotic, which can be genetically engineered to express a polypeptide which is not expressed by the non-engineered organism. In certain embodiments the host cell is selected from the group consisting of CHO cells, NS0 cells, SP2/0 cells, COS cells, K562 cells, BHK cells, PER C6 cells and HEK cells. The host cell may be a bacterial cell selected from the group consisting of *E. coli* (for example W3110, BL21), *B. subtilis* and/or other suitable eukaryotic cells, such as fungal or yeast cells (e.g., *Pichia pastoris, Aspergillus* sp., *Saccharomyces cerevisiae, Schizosaccharomyces pombe, Neurospora crassa*).

As used herein, the terms "host cell protein" and the abbreviation "HCPs" are used interchangeably and refer to any polypeptides, aside from the immunoglobulin (i.e. protein of interest) which the host cell has been engineered to express, which is expressed by the host cell.

As used herein, the term "process impurities" may be defined as per International Council for Harmonisation of Technical Requirements for Registration of Pharmaceuticals for Human Use (ICH) guidelines (e.g. ICH Q6B), and is taken to refer to impurities that are present as a result of the process in which the protein of interest is produced. Therefore, this definition encompasses impurities that are derived from the manufacturing process, i.e., cell substrates (e.g., host cell proteins, host cell DNA/RNA), cell culture (e.g., inducers, antibiotics, or media components), or downstream processing thereof. The term "process impurities" does not include product related impurities (e.g. antibody aggregates and/or fragments).

All "amino acid" residues identified herein may be in the natural L-configuration. In keeping with standard polypeptide nomenclature, abbreviations for amino acid residues are as shown in Table 2:

TABLE 2

Amino acid abbreviations

| One Letter Abbreviation | Three Letter Abbreviation | Amino Acid |
| --- | --- | --- |
| K | Lys | Lysine |
| N | Asn | Asparagine |
| T | Thr | Threonine |
| R | Arg | Arginine |
| M | Met | Methionine |
| I | Ile | isoleucine |
| Q | Gln | Glutamine |
| H | His | Histidine |
| P | Pro | Proline |
| E | Glu | Glutamate |
| D | Asp | Aspartate |
| A | Ala | Alanine |
| G | Gly | Glycine |
| V | Val | Valine |
| Y | Tyr | Tyrosine |
| S | Ser | Serine |
| W | Trp | Tryptophan |

TABLE 2-continued

Amino acid abbreviations

| One Letter Abbreviation | Three Letter Abbreviation | Amino Acid |
|---|---|---|
| C | Cys | Cysteine |
| L | Leu | Leucine |
| F | Phe | Phenylalanine |

All amino acid sequences are detailed herein by formulae whose left to right orientation is in the conventional direction of amino-terminus to carboxy-terminus.

As used herein, the term "germline" as used in the context to describe the amino acid sequence of an antibody, describes the amino acid sequence of any antibody obtained from a system using human immunoglobulin sequences through, for example, immunizing a transgenic mouse carrying human immunoglobulin genes or by screening a human immunoglobulin gene library, and wherein the selected human antibody is at least 90% identical in amino acid sequence to the amino acid sequence encoded by the germline immunoglobulin gene.

As used herein, when referring to "conserved germline to germline amino acids changes", this is defined as a conservative change to an antibody wherein at least one amino acid of the initial germline sequence of the antibody is modified to different amino acid sequence derived from the aligned, equivalently positioned amino acid of another antibody germline sequence of the same species.

As used herein, the terms "parent" or "parental" in the context of describing an antibody, refer to any immunoglobulin which is comprised of an amino acid sequence of a naturally occurring, germline human immunoglobulin. The terms "parent" or "parental" in the context of describing an antibody of the IgG4 subclass refers to any immunoglobulin which contains the naturally occurring human germline amino acid sequence for the conserved constant regions in both the heavy and light chain, of a human IgG4 molecule along with any amino acid sequence in the variable domain including the complementarity determining region, and in which the hinge region contains the amino acid sequence; cysteine-proline-proline-cysteine or cysteine-proline-serine-cysteine.

As used herein, the terms "modified IgG4" or "variant IgG4" or "recombinant IgG4" are used interchangeably and refer to any IgG4 antibody which comprises the same amino acid sequence as a "parent" IgG4 antibody, but differs in one or more amino acids. In certain embodiments, these differences may constitute at least one of the modifications detailed in Table 1, or as described herein.

As used herein, the term "binding" in the context of the binding of an antibody to a host cell protein (HCP), such as PLBL2, refers to both the specific and/or non-specific, reversible and irreversible interactions between the antibody and said host cell protein (HCP). "Level of binding", "ability to bind", "propensity for interaction", "interaction" are herein used interchangeably. Such binding interactions between the antibody and the HCP can be quantitatively determined by a person skilled in the art. For example, an anti-PLBL2 Western Blot can be carried out as in Example 2.

Such binding interactions can also be quantitatively determined by, for instance, using surface plasmon resonance (SPR) technology in a BIAcore™ 3000 or BIAcore™ T200 instrument using the antibody as the ligand and the host cell protein as the analyte.

As used herein, the term "affinity" refers to the strength of binding of one molecule, e.g. an antibody of the invention to HCP, such as PLBL2. The binding affinity of an antibody to its target or a contaminant (such as HCP) may be determined by equilibrium methods. Methods to quantitate binding affinity include Bio Layer Interferometry (BLI), for example in combination with an Octet® RED 384 instrument (see Example 6). Other methods include enzyme-linked immunoabsorbent assay (ELISA) or radioimmunoassay (RIA)), or kinetics (e.g. BIACORE™ analysis).

As used herein, the term "activity" in the context of the binding of an antibody to a host cell protein, such as PLBL2, refers to the amount of HCP that is binding to the antibody. For example, the number of antibodies which are bound to PLBL2. Methods to quantitate binding activity include: enzyme-linked immunoabsorbent assay (ELISA) to determine how much HCP binds to the antibody (for example PLBL2 ng/mg), see Example 3; surface plasmon resonance (SPR) technology in a BIAcore™ 3000 or BIAcore™ T200 instrument to determine how much HCP binds to the antibody (for example PLBL2 binding (RU)), see Example 4.

As used herein, the term "reduced" when used in the context of describing a change in the binding of one antibody to a host cell protein compared to the binding of another antibody to the same host cell protein, refers to the relative difference in binding of the two antibodies to said host cell protein. The difference in affinity or activity can be quantitatively determined by for instance, using surface plasmon resonance (SPR) technology in a BIAcore™ 3000 or BIAcore™ T200 instrument using the antibody as the ligand and the host cell protein as the analyte, in which case, one antibody is defined as having a "reduced" level of binding compared to another, if there is a greater than 10% reduction in binding activity and/or a greater than 10-fold reduction in binding affinity. Therefore, in one embodiment, the variant antibody has at least a 10% reduction in binding activity and/or at least a 10-fold reduction in binding affinity compared to the unmodified antibody.

As used herein, the term "parts per million" or "ppm" in the context of describing the concentration or amount of a component, such as PLBL2, refers to the concentration of said component relative to the concentration of the product, such as an IgG4 antibody. The "ppm" value is essentially the molar ratio between a component and the antibody product and can be calculated for example by dividing the concentration of the component (measured in ng/mL) by the concentration of the antibody (measured in mg/mL). The result of this calculation is then the parts of the component per million parts of the antibody product. Alternatively, the HCP detected can be measured by "ppb" ("parts per billion") which is equivalent to pg/mg.

As used herein, "affinity chromatography" is a chromatographic method that makes use of the specific, reversible interactions between biomolecules rather than general properties of the biomolecule such as isoelectric point, hydrophobicity, or size, to effect chromatographic separation.

"Superantigen" refers to generic ligands that interact with members of the immunoglobulin superfamily at a site that is distinct from the target ligand-binding sites of these proteins. Staphylococcal enterotoxins are examples of superantigens which interact with T-cell receptors. Superantigens that bind antibodies include, but are not limited to, Protein G, which binds the IgG constant region; Protein A which binds the IgG constant region and VH domains; and Protein L which binds VL domains. Therefore, in one embodiment the superantigen is selected from the group consisting of Protein A, Protein G, and Protein L.

When used herein, the term "Protein A" encompasses Protein A recovered from a native source thereof (e.g., the cell wall of *Staphylococcus aureus*), Protein A produced synthetically (e.g. by peptide synthesis or by recombinant techniques), and variants thereof which retain the ability to bind proteins which have a $C_H2/C_H3$ region.

"Protein A affinity chromatography" or "Protein A chromatography" refers to a specific affinity chromatographic method that makes use of the affinity of the IgG binding domains of Protein A for the Fc portion of an immunoglobulin molecule. This Fc portion comprises human or animal immunoglobulin constant domains $C_H2$ and $C_H3$ or immunoglobulin domains substantially similar to these. In practice, Protein A chromatography involves using Protein A immobilized to a solid support. Protein G and Protein L may also be used for affinity chromatography. The solid support is a non-aqueous matrix onto which Protein A adheres (for example, a column, resin, matrix, bead, gel, etc). Such supports include agarose, sepharose, glass, silica, polystyrene, collodion charcoal, sand, polymethacrylate, cross-linked poly(styrene-divinylbenzene), and agarose with dextran surface extender and any other suitable material. Such materials are well known in the art. Any suitable method can be used to affix the superantigen to the solid support. Methods for affixing proteins to suitable solid supports are well known in the art. Such solid supports, with and without immobilized Protein A or Protein L, are readily available from many commercial sources including such as Vector Laboratory (Burlingame, Calif.), Santa Cruz Biotechnology (Santa Cruz, Calif.), BioRad (Hercules, Calif.), Amersham Biosciences (part of GE Healthcare, Uppsala, Sweden) and Millipore (Billerica, Mass.).

The term "buffer" means a buffering solution or a buffering agent that stabilizes the pH of a solution. A buffer generally comprises a weak acid and its conjugate base, or a weak base and its conjugate acid. Buffering of a protein solution at or close to the optimal pH helps to ensure proper protein folding and function.

The term "fatty acid ester" means any organic compound that contains a fatty acid chain linked to a head group via an ester bond. An ester bond is formed when a hydroxyl group (e.g., an alcohol or carboxylic acid) is replaced by an alkoxy group. Examples of fatty acid esters generally include phospholipids, lipids (e.g., the head group is glycerol, including monoglycerides, diglycerides, and triglycerides), and surfactants and emulsifiers, including for example polysorbates like Polysorbate 20, Polysorbate 60, and Polysorbate 80, which are non-ionic detergents. Surfactants and emulsifiers are useful as cosolvents and stabilizers, and can be added to protein formulations to enhance protein stability against mechanical stress, such as air/liquid interface and solid/liquid interface shear.

The invention will now be described with reference to the following, non-limiting examples.

EXAMPLES

Example 1—HCP ELISA Dilutional Linearity of Final Bulk mAbs

Previous studies have shown that the host cell protein (HCP) phospholipase B-like 2 (PLBL2) may be present in antibody samples which have been generated using a mammalian cell host. Furthermore, the presence of PLBL2 may cause dilutional non-linearity to be observed when quantifying total HCP levels in a sample by ELISA. In an attempt to identify mAb products that might contain PLBL2 in the Final Bulk Drug Substance, a HCP ELISA was performed to assess for dilutional linearity of the samples. A proprietary ELISA was developed in-house to quantify the total amount of immunogenic HCP in CHO-derived product samples. This HCP ELISA uses custom goat anti-CHO HCP polyclonal antibodies and an in-house produced HCP reference standard, for multi-product use across CHO-derived products at GSK, and has been used as a platform method for monitoring the clearance of HCPs across purification process samples for multiple biopharmaceutical mAb products. This assay has a sensitivity of 2.0 ng/mL. The intermediate precision for in-process and final bulk substance samples ranges from 5.7-14.9% CV and the repeatability ranges from 3.5-8.8% CV.

A minimum of four dilutions of each sample are analyzed by ELISA. The adjusted HCP values are calculated for each dilution by multiplying the measured HCP concentration by the dilution factor, and then dividing by the product concentration. The adjusted HCP values for each sample dilution are plotted as a function of dilution factor on a log-log scale. The dilutional slope of each sample is calculated using the following log-log equation:

$$\text{Log(adjusted HCP)}=A+B*\text{Log(dilution factor)}$$

where A is the y-intercept and B is the slope. An increasing adjusted HCP value with increasing dilution is indicative of dilutional non-linearity, and might suggest the presence of PLBL2.

Humanized IgG products of different subtypes were analyzed, including IgG1, IgG2, IgG4, and an IgG2/IgG4 chimera. The IgG2/IgG4 chimera is an antibody with a human IgG4 germline sequence, albeit with the hinge region swapped for that of a human IgG2. The results demonstrate that dilutional non-linearity is only observed with mAb7, the IgG4 molecule (FIG. 1), as determined by the increasing adjusted HCP value with increasing dilution factor. Table 3 below contains the dilutional slope values obtained for each of these mAb products in the HCP ELISA.

TABLE 3

Dilutional slope values obtained for different mAb products in the HCP ELISA.

| Product | Isotype | Slope |
|---------|---------|-------|
| mAb1 | IgG1 | 0.013 |
| mAb3 | IgG2 | 0.002 |
| mAb4 | IgG2/4 | −0.014 |
| mAb7 | IgG4 | 0.416 |

These results suggest there is a HCP in the mAb7 Final Bulk substance that is in excess and saturating the anti-CHO HCP detection antibodies used in the ELISA. In order to confirm if the HCP is PLBL2, further experimentation was required.

Example 2—Anti-PLBL2 Western Blot of Different mAbs

Example 1 demonstrated that mAb7 exhibits dilutional non-linearity in the HCP ELISA. In order to determine if PLBL2 might be responsible for the dilutional non-linearity, an anti-PLBL2 western blot was performed on the same humanized IgG products previously analyzed by ELISA (Example 1).

Samples containing 100 μg of mAb product were diluted 1:1 with 2× sample buffer (Novex), and then loaded into a 4-20% gradient gel (Novex). SDS-PAGE was performed under constant current at 24 mA per gel for 30 minutes, followed by 36 mA per gel for 50 minutes. After electrophoresis, the gels were fixed and the proteins were stained with SYPRO® Ruby (Thermo Fisher Scientific). Sypro® RUBY stained gels were imaged on an FLA-3000 Fluorescent Image Analyzer (Fujifilm Corp.) The Sypro® RUBY image (FIG. 2A) demonstrates equal loading of each of the products onto the gel.

Western blotting was performed by transferring gels to PVDF membranes (Bio-Rad) using XCell II™ Blot Module (Novex), running at a constant voltage of 25V for 105 minutes. After transfer, the membranes were blocked overnight using Fluorescence blocking buffer (Rockland Immunochemicals) diluted 1:10 with TBST (Sigma). After blocking, the membranes were washed with TBST and incubated with anti-PLBD2 polyclonal antibody (Abcam, ab138334) at 1 µg/mL for two hours at room temperature. After incubation, the membranes were washed three times for 10 minutes with TBST. The membranes were then incubated with mouse anti-Rabbit cy3 conjugate (Jackson Immunoresearch) at 1 µg/mL for one hour at room temperature. After incubation, the membranes were washed three times for 10 minutes with TBST. After washing, the membranes were allowed to dry for 30 minutes. The dried membranes were imaged on an FLA-3000 Fluorescent Image Analyzer. This western blot has a lower limit of detection of 20 ng of PLBL2. The western blot image (FIG. 2B) demonstrates that PLBL2 is detected in the Final bulk substance for mAb7 and not any of the other IgG products. This result supports the argument that PLBL2 is responsible for the dilutional non-linearity observed for mAb7, described in Example 1, and further analysis should be performed to quantify the amount of PLBL2 present in the sample.

Example 3—Quantitation of PLBL2 in mAb Samples

Given the detection of PLBL2 in mAb7, an ELISA was developed in order to accurately quantify the concentration of PLBL2 in the samples. This ELISA was developed in house and uses recombinant hamster PLBL2 as a reference standard, and custom in-house generated polyclonal anti-PLBL2 antibodies for detection. This assay has a sensitivity of 2.0 ng/mL. The intermediate precision for samples is 3.23% CV.

The PLBL2 ELISA was used to quantify PLBL2 concentrations in samples taken throughout the purification process for the four different mAb products previously investigated. The PLBL2 concentrations were determined after harvest, the following the first chromatography step (Step 1), and the final bulk drug substance (Final), and can be found in Table 4 below.

TABLE 4

PLBL2 concentrations in mAb purification samples quantified by PLBL2 ELISA.

| Product | Isotype | PLBL2 (ng/mg) | | |
|---------|---------|---------|--------|-------|
|         |         | Harvest | Step 1 | Final |
| mAb1    | IgG1    | 3020.9  | 2.41   | 0.7   |
| mAb3    | IgG2    | x       | <0.1   | <0.1  |
| mAb4    | IgG2/4  | x       | 1.27   | <0.1  |
| mAb7    | IgG4    | 1228.4  | 600.9  | 236.4 |

The results found in Table 4 demonstrate that a substantial amount of PLBL2 remains in the final bulk drug substance of mAb7, but not the other mAb products tested. Interestingly, only 52% of the PLBL2 in the harvest material is removed during the first chromatographic purification step for mAb7, while 99.92% is removed from mAb1 during this step. Given that both products use the same resin for purification, it is likely that PLBL2 is interacting with the mAb molecule directly and not the chromatography resin.

Example 4—Binding of PLBL2 to Different mAbs by SPR

Based on the previous data, one likely explanation is that PLBL2 preferentially binds to mAb7 and not the other mAb products. As previously noted, mAb7 is an IgG4 molecule, which might provide a binding site for PLBL2 that is not present in the other subtypes. In order to further investigate why PLBL2 is not removed during purification for mAb7, a surface plasmon resonance (SPR) binding experiment was performed. In this experiment, anti-human IgG Fc antibody (GE Healthcare) was immobilized to two flow cells (FC4 and FC3) of a Series S CM5 sensor chip (GE Healthcare) using a Biacore™ T200 instrument (GE Healthcare) to a level of ~7000 response units (RU). The immobilized antibody was used to capture mAb products in 1×HBS-EP+ buffer (GE Healthcare) to a level of ~2500 RU onto FC4, using FC3 as an in line reference cell for background subtraction. Recombinant hamster PLBL2 was diluted to 5 µM using HBS-EP+ buffer, and injected for 60 seconds at 30 µL/minute. Dissociation of PLBL2 was measured for 180 seconds before regeneration of the surface using the manufacturer's recommended protocol.

Seven different humanized IgG products of different subtypes were analyzed for PLBL2 binding by SPR using this protocol, including IgG1, IgG2, IgG4, and an IgG2/IgG4 chimera (see Table 5, below). The results demonstrate that PLBL2 binds to all three IgG4 molecules tested, and does not bind to any of the other subtypes (FIG. 3B, FIG. 3C), despite nearly equal capture of the mAb on the sensor chip (FIG. 3A). PLBL2 binding levels to each mAb can be found in Table 5 below.

TABLE 5

PLBL2 binding levels to mAb products by SPR.

| Product | Isotype | PLBL2 Binding (RU) |
|---------|---------|--------------------|
| mAb1    | IgG1    | 7.2                |
| mAb2    | IgG1    | 7.1                |
| mAb3    | IgG2    | 5.0                |
| mAb4    | IgG2/4  | 4.2                |
| mAb5    | IgG4    | 98.4               |
| mAb6    | IgG4    | 100.1              |
| mAb7    | IgG4    | 103.6              |

The results in Table 5 show that PLBL2 has an increased propensity to bind to antibodies of the IgG4 subtype. Furthermore, as mAbs 2, 3, 5 and 6 all contain the same variable region, the results would indicate that it is the constant region of the IgG4 molecule which is responsible for its enhanced ability to bind PLBL2.

Notably, PLBL2 did not bind to mAb4, which is an IgG2/IgG4 chimera that contains the germline hinge region of an IgG2, whilst the remainder of the constant region is comprised of that of an IgG4. These results suggest that PLBL2 is not removed during purification of mAb7 due to directly binding to the mAb product.

These results would indicate that not only are the constant domains of the IgG4 molecule predominantly responsible for driving the binding of PLBL2, but that it is the hinge region of this constant domain which is likely responsible for the binding of PLBL2.

In order to calculate the binding affinity of the recombinant PLBL2 to mAb7, a second SPR experiment was performed. This experiment used the same immobilized anti-Human IgG Fc chip, but only captured mAb7 to a level of ~170 RU. After capture, PLBL2 was injected for 120 seconds at 30 µL/minute, with separate injections for concentrations ranging from 1.25 µM to 80 µM. The binding affinity ($K_D$) was determined using Biacore T200 evaluation software, using a 1:1 binding model at steady state.

The results demonstrate an increased binding of PLBL2 to mAb7 with increasing concentration (FIG. 4A). The binding response at steady state (~110 seconds after PLBL2 injection start) was used to calculate the binding affinity (FIG. 4B). A $K_D$ of 40.0 µM was calculated for PLBL2 binding to mAb7. While this is a relatively weak binding, this result was useful for setup of the HDX-MS experiment, in order to saturate the mAb7 molecule with PLBL2 in the experiment.

Example 5—Effect of Expression System on Binding of PLBL2

Previous examples have shown the increased propensity for antibodies of the IgG4 subtype to bind PLBL2, compared to other antibody subtypes (e.g. IgG1 and IgG2). A study was performed to determine whether the host cell expression system used to generate these antibodies can affect their ability to bind PLBL2. Studies were performed using mAb6 (an IgG4) and mAb3 (an IgG2), which both have the same variable domain but are of different IgG subclasses. Differences in the behaviour of these molecules can therefore be directly attributable to the constant antibody domains.

Briefly, CHO K1 and HEK293 cells expressing the IgG4 mAb6 (denoted mAb6A and mAb6B, respectively), were separately cultured, alongside another separate culture of CHO K1a cells expressing mAb3 (an IgG2). These cultures were harvested at an appropriate time-point before being passed through a standard mAb clarification and downstream purification process. Purified samples of each of these antibodies were then analysed and compared, for their ability to bind PLBL2, using Surface Plasmon Resonance (SPR) using a Biacore™ T200.

Samples (Table 6) were diluted to 20 µg/mL in HBS-EP buffer and injected over the active flow cell of a pre-immobilised protein A chip (GE Healthcare) for 60 seconds at 10 µL/min. PLBL2, diluted to 100 µg/mL in HBS-EP, was then injected over both the active flow cell and reference flow cell for 120 seconds at 5 µL/min. Both flow cells were regenerated using 10 mM Glycine pH 1.5 for 10 seconds at 30 µL/min and then HBS-EP for 30 seconds at 30 µL/min.

TABLE 6

Molecular format and host cell expression systems used to generate the antibodies

| Molecule number | Molecular Format and Host Cell Expression System |
|---|---|
| mAb3 | Human IgG2 (CHO K1) |
| mAb6A | Human IgG4 (CHO K1) |
| mAb6B | Human IgG4 (HEK 293) |

Results (FIG. 5) demonstrated that both IgG4 molecules interact comparably with PLBL2 despite being generated in different cell lines. The IgG2 molecule meanwhile does not interact. Table 7 demonstrates the arbitrary value generated by each sample.

TABLE 7

Binding of PLBL2 to IgG4 and IgG2 molecules expressed in different host systems

| Molecule number | Relative Response Unit |
|---|---|
| mAb3 | −1.0 |
| mAb6A | 119.2 |
| mAb6B | 118.8 |

Example 6—Quantitation of Binding Affinity of Antibodies of IgG2 and IgG4 Sub-Types Previous experiments have shown the increased ability for antibodies of the IgG4 subclass to bind PLBL2, compared to antibodies of other subclasses (e.g. IgG1 and IgG2). Studies were also performed to quantify the affinity of an antibody of an IgG4 for PLBL2.

Samples were generated as described in Example 5. The affinity of PLBL2 binding with the antibody in these samples, was then assessed by Bio Layer Interferometry (BLI) using an Octet® RED 384 instrument. Samples (the same as referred to in Table 6) were diluted to 10 µg/mL in PBS-T. Commercially available protein A biosensors (Pall) were dipped into each sample for 120 seconds at 1000 RPM. Loaded biosensors were then dipped into PLBL2 at various concentrations (1538 nM serially diluted 2 fold to 16 nM) for 300 seconds at 1000 RPM to assess association before being dipped into PBS-T for 300 seconds at 1000 RPM to assess dissociation. Biosensors were regenerated using 10 mM Glycine pH 1.5 and PBS-T as per manufacturer's instructions.

Results (Table 8) were generated using a local fit with a 1:1 binding model. Affinity data was not acquired for mAb3 as there was no interaction (FIG. 6A). Both mAb6A and mAb6B had low affinity; mAb6A had an approximately 14-fold increase in affinity over mAb6B due to a faster association rate. Dissociation rates meanwhile were similar. The fitting of mAb6A and mAb6B are demonstrated in FIGS. 6B and 6C, respectively.

These results show that whilst host cell expression system does not affect the ability of an expressed IgG4 to bind PLBL2, it may potentially impact upon the binding affinity of the molecule.

TABLE 8

Binding Affinity of IgG2 and IgG4 molecules

| Molecule number | KD (uM) | $k_{on}$ (1/Ms) | $k_{dis}$ (1/s) |
|---|---|---|---|
| mAb3 | N/A | N/A | N/A |
| mAb6A | 11.2 | 3.82E+05 | 5.26E−02 |
| mAb6B | 160 | 1.32E+04 | 5.63E−02 |

Example 7—Interaction Between mAb7 and PLBL2 Probed by HDX-MS

In order to have a further understanding of the science underlying interactions of mAb7 and PLBL2, HDX-MS analysis of mAb7 and mAb7 bound with PLBL2 samples were performed using a Waters HDX manager system coupled to a Synapt G2-S mass spectrometer. Based on the $K_D$ of 40.0 µM by SPR, ~70% of mAb is bound with PLBL2 after deuterium labelling. Deuterium labelling was measured at 0.5 min, 5 min, 60 min, 120 min, 180 min, and 240 min. The data were analyzed using Waters DynamX software and generated HDX differential plot (FIG. 7). Vertical sticks represent the total HDX differences of each peptide from six labelling time points. Comparison of the HDX profile of unbound and PLBL2-bound mAb7 reveals that region K218-F256 in heavy chain show a reduction in deuterium uptake upon binding to PLBL2. This indicates a stabilization of this region due to PLBL2 binding to mAb7 and correlates well with other experimental binding results.

Example 8—Sequence Alignment of the Hinge Region of Different mAbs

The previous results demonstrate that PLBL2 contaminates mAb7 (an IgG4 molecule) by directly binding to the product and co-purifying. Similarly, previous examples have shown that mAb5 and mAb6, which are also of the IgG4 subtype, are also capable of binding PLBL2. Analysis of PLBL2 binding to mAbs of different isotypes suggested that the binding most likely occurs in the hinge region of the IgG4 molecule, which was supported by HDX-MS data. Given the small number of different amino acids in the different IgG isotypes, it is likely that individual amino acid residues that are involved in PLBL2 binding might be identified. In order to determine the IgG4 amino acid residues involved in PLBL2 binding, an amino acid sequence alignment of the hinge region of the mAb products was generated.

In analyzing the sequence alignment, residues of interest are those that are conserved in the IgG4 molecules (mAb5, mAb6 and mAb7), in which PLBL2 was observed to bind to, and not conserved (i.e. a different residue) in the other IgG subtypes, in which PLBL2 did not bind. This analysis yielded 10 such residues, which are outlined by a black box (FIG. 8). Specifically, the residues of interest are: K203, R222, S227, Y229, G230, P237, P238, E246, F247 and E248.

Mutation of these 10 residues from the amino acid found in IgG4 to that found in IgG2 or IgG1 were expected to prevent PLBL2 from binding to the IgG4 molecule.

Example 9—Mutagenesis of IgG4 Hinge Region Residues to Mitigate Binding to PLBL2

The studies detailed in Examples 1 through to 8 have shown that the constant region of the IgG4 molecule is predominantly responsible for enabling the binding of these immunoglobulins to PLBL2. Furthermore, comparisons made between an IgG4 and an IgG2/IgG4 chimera have allowed these interactions with PLBL2 to be localised at or nearby the hinge region of the molecule. Alignment of the amino acid sequences of the various molecules which have been studied, has allowed through a process of elimination, the specific amino acids within the hinge region which play a role in PLBL2 binding to be identified. The final step is to perform confirmatory mutagenesis experiments to show how the modification of the hinge region of an IgG4 molecule can mitigate the binding of this subclass of immunoglobulins to PLBL2.

Studies were performed in which 7 of the 10 amino acid residues identified as being responsible for causing the binding of PLBL2 to antibodies of the IgG4 subclass, were substituted for alternate amino acids, such as those which are found in the germline hinge sequence of human IgG1 and/or IgG2 antibodies. Using mAb5 as a model molecule, mutagenesis experiments in which a HEK293 host cell expression system was transiently transfected with vector DNA encoding for a number of mAb5 variants, with a modified hinge region, were carried out.

Mutations to the hinge region of mAb5 were at amino acid sequence positions which were previously identified to have some role in influencing PLBL2 binding (Example 8). Mutations were introduced as either single point mutations, as have been described in Table 1, as well as in various combinations thereof, resulting in the generation of 7 different hinge modified IgG4 variant molecules (mAb5-1B, 2B, 3B, 4B, 6B and 7B). In parallel, a culture was also set up to transiently express the unmodified parent IgG4 (mAb5B). In addition to this, mutations to the hinge region of mAb7, also an IgG4 albeit directed against a different antigen target, were also made, either as single point mutations, as well as in various combinations thereof resulting in the generation of 3 different hinge modified variants (mAb7-2B, 4B and 5B).

The suffix numbering of these variants reflect the mutations that were made and the numbering has been maintained across both sets of hinge modified IgG4 variants. Thus the hinge region of mAb5-2B is the same as that of mAb7-2B.

Furthermore, cultures were also set up to express an IgG2 (mAb3B) and an IgG4 (mAb6B) as additional controls as well as a hinge modified IgG1 variant (mAb2-αB). FIG. 9 illustrates the modified hinge region of these IgG4 variants, and aligns them against the hinge region sequences of the other mAb molecules included in the study. Table 9 details the different molecules which were evaluated. The suffix "A" and "B" on the molecule names, denotes whether the antibody was expressed in CHO K1 or HEK293 cells, respectively.

TABLE 9

Details of IgG1, IgG2, IgG4 and IgG4 variants evaluated

| Molecule Name | Modification | Molecule Type |
|---|---|---|
| mAb2-aB | Substitution of K222R | HEK293 expressed hinge modified IgG1 variant |
| mAb3B | | HEK293 expressed IgG2 |
| mAb5B | | HEK293 expressed IgG4 |
| mAb5-1B | Substitution of K203Q | HEK293 expressed hinge modified IgG4 variant |

TABLE 9-continued

Details of IgG1, IgG2, IgG4 and IgG4 variants evaluated

| Molecule Name | Modification | Molecule Type |
|---|---|---|
| mAb5-2B | Substitution of R222K | HEK293 expressed hinge modified IgG4 variant |
| mAb5-3B | Substitution of S227P | HEK293 expressed hinge modified IgG4 variant |
| mAb5-4B | Substitution of R222K and S227P | HEK293 expressed hinge modified IgG4 variant |
| mAb5-5B | YGPP (SEQ ID NO: 23) deleted CCVE (SEQ IG NO: 25) inserted | HEK293 expressed hinge modified IgG4 variant |
| mAb5-6B | YGPP (SEQ ID NO: 23) deleted SCDKTHT (SEQ ID NO: 24) inserted | HEK293 expressed hinge modified IgG4 variant |
| mAb5-7B | Substitution of E226L | HEK293 expressed hinge modified IgG4 variant |
| mAb5-8B | Substitution of R222T | HEK293 expressed hinge modified IgG4 variant |
| mAb6B | | HEK 293 expressed IgG4 |
| mAb7A | | CHO K1 expressed IgG4 |
| mAb7-2B | Substitution of R222K | HEK293 expressed hinge modified IgG4 variant |
| mAb7-4B | Substitution of R222K and S227P | HEK293 expressed hinge modified IgG4 variant |
| mAb7-5B | YGPP (SEQ ID NO: 23) deleted CCVE (SEQ IG NO: 25) inserted | HEK293 expressed hinge modified IgG4 variant |
| mAb8A | | CHO K1 expressed IgG1 |

The material generated by the HEK293 cells was purified using a standard mAb purification process. Briefly, following culturing for an appropriate period for sufficient transient expression of the product mAbs, cells were removed and the clarified cell culture supernatant was purified using Protein A affinity chromatography. The Protein A eluate was titrated to a neutral pH using a Tris solution. The neutralised protein A eluates containing the different mAb molecules under study were then subjected to a series of binding assays as are described in Examples 10 to 12.

Example 10—PLBL2 Interaction Assay on IgG2, IgG4 and IgG4 Variant Molecules

Interaction of various mAbs generated and described in Example 9, with recombinant human PLBL2 was assessed by Surface Plasmon Resonance (SPR) using a Biacore™ T200 (GE Healthcare) binding method. 20 µg/mL of mAb was injected over flow cell 4 of a commercially available pre-immobilised protein A chip (GE Healthcare) for 60 seconds at 10 µL/min and allowed to stabilise in HBS-EP+ running buffer for 10 seconds. The variation of the level of captured antibody was less than 10%. 100 µg/mL (1538 nM) recombinant human PLBL2 was then injected over flow cells 4 and 3 for 120 seconds at 5 µL/min. Flow cell 3 acts as an in-line reference cell, the reduced 5 µL/min flow rate was used to encourage low affinity interactions. The sensor was then regenerated with 10 mM Glycine pH 1.5 for 10 seconds at 30 µL/min.

Based on the results of prior experiments, mAb8A (which is an IgG1) was known to have no interaction with recombinant human PLBL2. As such it was used as a negative control to which results were normalised.

The results of the SPR analysis (FIG. 10) indicate a roughly 90% decrease in RU's of PLBL2 to mAb5-2B and mAb5-4B compared to their parent molecule (mAb5B), and approximately 80% drop in RU's of PLBL2 to mAb7-2B and mAb7-4B compared to their parent molecule (mAb7A). mAb5-3B demonstrated no change in binding, indicating this mutation alone was unsuccessful at reducing interaction. mAb5-2B contains a single amino acid substitution in position 222 from arginine to lysine. mAb5-3B contains a single amino acid substitution in position 227 from serine to proline. mAb5-4B contains the mutations present in both mAb5-2B and mAb5-3B; indicating that whilst the proline substitution in position 227 is not reducing PLBL2 interaction, it is also having no adverse affect, and that the reduction in PLBL2 binding observed is due to the lysine substitution at position 222. Indeed, substitution of the lysine at position 222 in mAb2 (FIG. 9) to an arginine, representing an IgG1 to IgG4 germline switch at this position, resulted in a mutant (mAb2-αB) with increased binding to PLBL2 by SPR, when compared to the parent molecule (mAb2) which displayed no binding to PLBL2. Switching the arginine at position 222 in mAb5 (FIG. 9) to a threonine, representing an IgG4 to IgG2 germline switch at this position, resulted in a mutant (mAb5-8B) with approximately 30% decreased binding to PLBL2 by SPR, compared to the parent molecule (mAb5).

Whilst this data suggest the arginine at position 222 is a significant factor in facilitating PLBL2 binding, other hinge residues can also influence binding of this HCP, as evidenced by the reduced PLBL2 binding exhibited by mAb5-5B (FIG. 10). Meanwhile mAb8A demonstrated no interaction with PLBL2; mAb6B demonstrated the largest amount of binding.

Example 11—PLBL2 Affinity Assay on IgG2, IgG4 and IgG4 Variant Molecules

The affinity of the interaction of PLBL2 to the various mAbs generated and described in Example 9, were tested in the same manner described in Example 6, by Biolayer Interferometry (BLI) using an Octet® RED 384 instrument (ForteBio).

Commercially available protein A biosensors were dipped into samples at 10 µg/mL for 120 seconds at 1000 RPM. Biosensors were dipped into assay buffer (HBS-EP+) for 30 seconds at 1000 RPM to allow dissociation of loosely bound protein. The loaded biosensors were then dipped into recombinant human PLBL2 at various concentrations (1538, 769.2, 384.6, 192.3, 96.15, 48.15, 24, 0 nM) and finally dipped into HBS-EP+ for 5 minutes.

The association and dissociation rates were measured using a 1:1 binding model with a global fit; however only the first 50 seconds of the dissociation curve were analysed due to a fast off rate. Results are demonstrated in Table 10.

TABLE 10

Binding Affinity of IgG1, IgG2, IgG4 and IgG4 variant molecules

| Sample ID | $K_D$ (M) | Fold Change in KD (compared to parent molecule) | $k_{on}$ (1/Ms) | $k_{dis}$ (1/S) |
|---|---|---|---|---|
| mAb5B | 1.83E−05 | n/a | 1.90E+03 | 3.46E−02 |
| mAb5-1B | 1.16E−05 | −0.4 | 3.44E+03 | 4.00E−02 |
| mAb5-2B | | Fitting unavailable | | |
| mAb5-3B | 1.77E−04 | 8.7 | 2.27E+02 | 4.03E−02 |
| mAb5-4B | | Fitting unavailable | | |
| mAb5-5B | 1.28E−04 | 6.0 | 2.15E+02 | 2.74E−02 |
| mAb5-6B | 6.30E−04 | 33.5 | 4.95E+01 | 3.12E−02 |
| mAb5-7B | 3.16E−06 | −0.8 | 3.99E+03 | 1.26E−02 |
| mAb6B | 4.20E−04 | 22.0* | 1.48E+02 | 6.19E−02 |
| MAb7A | 3.17E−05 | n/a | 1.70E+03 | 5.39E−02 |
| mAb7-2B | | Fitting unavailable | | |
| mAb7-4B | | Fitting unavailable | | |
| mAb7-5B | 2.65E−04 | 8.4 | 3.68E+02 | 9.74E−02 |
| mAb8A | | Fitting unavailable | | |

*fold change calculated based on $K_D$ of mAb5B

No kinetic value could be calculated for mAb5-2B, mAb5-4B, mAb7-2B, mAb7-4B and mAb8A due to poor curve fitting, indicative that there was no interaction to PLBL2 for these molecules. These results concur with findings from Example 10, which also demonstrate impacted binding to PLBL2 for these samples. A large reduction in $K_D$ (above 10×) was seen for mAb5-6B compared to the parent molecule (mAb5B). mAb5-1B and mAb5-7B demonstrated slightly increased affinity to PLBL2 due to a slightly faster association rate ($k_{on}$), which is undesirable. All remaining mutants demonstrated less than 10× reduction in binding to PLBL2 when compared to the parent molecule and as such the change in binding affinity was not considered significant.

Example 12—Antigen Binding of IgG2, IgG4 and Variant IgG4 Molecules

The antibody molecules mAb3, mAb5 (including all of the hinge modified variants) and mAb6 all comprise the same variable region, as these antibodies are targeted against the same antigen. In order to demonstrate that sample mutagenesis had no adverse affect on antigen binding activity of each molecule, antigen binding was assessed by Surface Plasmon Resonance (SPR) using a Biacore™ T200 (GE Healthcare). Activity was assessed by using a pre-immobilised protein A sensor (GE Healthcare) to capture the ligand. 5× start up cycles were run over all flow cells in order to regenerate the sensor surface (using 10 mM glycine pH 1.5 for 60 seconds at 30 µL/min) prior to use. Each mAb sample was diluted 10 µg/mL in PBS-T and injected onto flow cell 4 for 60 seconds at 10 µL/min, with a stabilisation period of 10 seconds. 10 µg/mL of target antigen was then injected for 60 seconds at 10 µL/min over flow cells 4 and 3, after which the injection was stopped and assay buffer was injected at a flow rate of 10 µL/min for 100 seconds to allow for dissociation. The sensor surface was then regenerated using 10 mM glycine pH 1.5 for 60 seconds at 30 µL/min, ready for the next injection.

To calculate the activity of each molecule, the antigen binding response (RU's) was divided by the antibody capture response (RU's) and reported as a percentage. The reported percentage indicates the amount of antibody present in a sample which is still able to bind to its antigen. The assay error attributed to this experiment is 10%. Table 11 shows that all mAbs demonstrated 100±10% activity to the target antigen, indicating that there has been no loss or change in binding. All mutants performed comparably. In particular, there was no difference in the binding of mAb5B or any of its hinge modified variants (mAb5-1B to 7B).

TABLE 11

Binding of IgG2 and IgG4 subclasses of each mAb to a target antigen

| Sample Id | % Binding |
|---|---|
| mAb3B | 103.1% |
| mAb5B | 94.3% |
| mAb5-1B | 95.3% |
| mAb5-2B | 95.0% |
| mAb5-3B | 93.4% |
| mAb5-4B | 95.1% |
| mAb5-5B | 94.9% |
| mAb5-6B | 94.8% |
| mAb5-7B | 97.3% |
| mAb6B | 94.2% |

Example 13—Mitigation of IgG4 Binding to Host Cell Proteins (HCPs)

Problematic host cell proteins typically co-purify with the product and whilst usually are present in only trace amounts, there have been cases in which the levels present in the fully purified drug substance can present both a safety and drug efficacy issue. Whilst the binding of PLBL2 presents an important example of this, there have been cases reported of other problematic host cell proteins interacting with the antibody product of interest.

As a result, studies can be performed in order to demonstrate the effect of the IgG4 hinge region modifications to mitigate the binding of other HCPs. The first stage will be to identify HCPs which have a propensity to interact with an IgG4, for example using mAb6 as a model molecule. These HCPs can be identified using a HCP enrichment method whereby the Fc region of the mAb will bind to commercially available protein A beads and undergo multiple 10 minute incubation periods with null CHO K1 clarified unprocessed bulk (CUB) material. The final bound complex is then eluted from the beads and analysed using LC-MS/MS. A multiple reaction monitoring (MRM) method can be used to quantify present host cell proteins.

Once these HCPs have been successfully identified, the methods detailed in previous Examples can be used to assess the binding of these HCPs to both the original mAb5 molecule, along with the modified mAb5 mutants, the generation of which are described in Example 9. These studies will serve to illustrate the ability to not only mitigate PLBL2 binding to IgG4 using the hinge region modifications which are the subject of this invention, but also to more broadly reduce the propensity for binding to HCPs more generally.

The invention claimed is:

1. A variant IgG4 antibody comprising a modified heavy chain constant region, wherein the variant IgG4 antibody has a reduced level of binding to host cell protein (HCP), compared to an unmodified IgG4 antibody,
   wherein the modified heavy chain constant region comprises substitution of Kabat residue R222 to T, K or Q; and/or
   replacement of YGPP (SEQ ID NO: 23) (Kabat residues 229 to 238) with CCVE (SEQ ID NO:25).

2. The variant IgG4 antibody according claim 1, wherein the IgG4 antibody has reduced binding affinity and/or binding activity to host cell protein (HCP) in comparison to the unmodified IgG4 antibody.

3. The variant IgG4 antibody according to claim 1, wherein the variant IgG4 antibody comprises a further substitution of S241 to P and/or L248 to E and/or replacement of EFLGGP (SEQ ID NO: 31) (Kabat residues 246 to 251) with PAAAP (SEQ ID NO: 33) or PAAAS (SEQ ID NO: 32).

4. The variant IgG4 antibody according to claim 1, wherein the variant IgG4 antibody comprises the sequence CPPC (SEQ ID NO: 20) (Kabat residues 239 to 242).

5. The variant IgG4 antibody according to claim 1, wherein no further modifications are made in the heavy chain constant region in comparison to the unmodified IgG4 antibody.

6. The variant IgG4 antibody according to claim 1, wherein the host cell protein is putative phospholipase B-Like 2 (PLBL2).

7. A cell line encoding the variant IgG4 antibody of claim 1.

8. A composition comprising the variant IgG4 antibody according to claim 1.

9. The composition according to claim 8, wherein the variant IgG4 antibody is at a concentration of at least 10 mg/mL, at least 20 mg/mL, at least 50 mg/mL, at least 75 mg/mL or at least 100 mg/mL.

10. The composition according to claim 8, wherein the composition further comprises a putative phospholipase B-Like 2 (PLBL2) and the concentration of the PLBL2 in the composition is less than 500 ppm, less than 100 ppm or less than 10 ppm.

11. The composition according to claim 8, which additionally comprises a buffer and/or a fatty acid ester; optionally wherein the fatty acid ester is Polysorbate 20 or Polysorbate 80.

12. The variant IgG4 antibody according to claim 1, wherein the modified heavy chain constant region further comprises a substitution of one or more amino acids wherein the substitution is Kabat residue K203 to R, E, or Q; Kabat residue E226 to L or I; Kabat residue S227 to R, P, A, N, or T; Kabat residue Y229 to S, C, F, W, or H; Kabat residue G230 to C, A, N, or S; Kabat residue P237 to H, E, D, or V; and/or Kabat residue P238 to T, K, or E.

13. The variant IgG4 antibody according to claim 1, wherein the modified heavy chain constant region further comprises a replacement of ESKYGPP (SEQ ID NO: 26) (Kabat residues 226 to 238) with EPKSCDKTHT (SEQ ID NO: 27), or ERKYGPP (SEQ ID NO: 28), or ERKCCVE (SEQ ID NO: 29), or ELKTPLGDTTHT (SEQ ID NO: 30).

14. The variant IgG4 antibody according to claim 1, wherein the modified heavy chain constant region further comprises a replacement of YGPP (SEQ ID NO: 23) (Kabat residues 229 to 238) with SCDKTHT (SEQ ID NO: 24).

* * * * *